United States Patent [19]

Kristiansen et al.

[11] Patent Number: 5,223,520
[45] Date of Patent: Jun. 29, 1993

[54] PYRIDINE COMPOUNDS WHICH ARE USEFUL AS PESTICIDES

[75] Inventors: Odd Kristiansen, Möhlin; Laurenz Gsell, Basel; Peter Maienfisch, Rodersdorf, all of Switzerland

[73] Assignee: Ciba-Geigy Corporation, Ardsley, N.Y.

[21] Appl. No.: 858,910

[22] Filed: Mar. 27, 1992

[30] Foreign Application Priority Data

Apr. 4, 1991 [CH] Switzerland ............... 1004/91

[51] Int. Cl.$^5$ ............... A01N 43/40; C07D 213/26
[52] U.S. Cl. ............... 514/357; 546/193; 546/275; 546/286; 546/287; 546/288; 546/289; 546/296; 546/297; 546/300; 546/312; 546/332; 514/318; 514/343; 514/344; 514/345; 514/348; 514/349; 514/351; 514/352
[58] Field of Search ............... 546/286, 287, 288, 289, 546/296, 297, 300, 334, 312, 192, 275, 332; 514/344, 345, 348, 349, 351, 352, 357, 318, 343

[56] References Cited

U.S. PATENT DOCUMENTS 4,806,553  2/1989  Shiokawa ............... 514/332

FOREIGN PATENT DOCUMENTS

| 0254859 | 2/1988 | European Pat. Off. ............... 546/266 |
| 0302389 | 2/1989 | European Pat. Off. ............... 546/290 |
| 0375907 | 7/1990 | European Pat. Off. ............... 546/290 |
| 0376279 | 7/1990 | European Pat. Off. ............... 514/344 |
| 0383091 | 8/1990 | European Pat. Off. ............... 514/344 |

*Primary Examiner*—C. Warren Ivy
*Assistant Examiner*—Zinna N. Davis
*Attorney, Agent, or Firm*—Kevin T. Mansfield; Edward McC. Roberts

[57] ABSTRACT

Compounds of formula $$A-CH(R_2)-N(R_1)-C(=X)-N(R_5)=C-N(R_3)(R_4) \quad (I)$$

wherein $R_1$ is hydrogen, $C_1$-$C_4$alkyl or $C_3$-$C_6$cycloalkyl, $R_2$ is hydrogen or $C_1$-$C_4$alkyl, $R_3$ is hydrogen, $C_1$-$C_4$alkyl or $C_3$-$C_6$cycloalkyl and $R_4$ is $C_1$-$C_4$alkyl, $C_3$-$C_6$cycloalkyl or —$CH_2CH_2COOR_7$, or $R_3$ and $R_4$ together are —$(CH_2)_4$— or —$(CH_2)_5$—, $R_5$ is hydrogen, $C_1$-$C_4$alkyl,

[phenyl ring with $R_6$ substituent],

—$CH_2OCH_3$, —$CN$, —$COOR_7$ or

—$CON(R_7)(R_8)$, $R_6$ is hydrogen, chlorine, methyl or nitro, $R_7$ and $R_8$ are each methyl or ethyl, A is an unsubstituted or mono- to tetra-substituted, aromatic or non-aromatic, monocyclic or bicyclic, heterocyclic radical, one or two substituents being selected from the group consisting of $C_1$-$C_3$haloalkyl, cyclopropyl, halocyclopropy, $C_2$-$C_3$alkenyl, $C_2$-$C_3$alkynyl, $C_2$-$C_3$haloalkenyl, $C_2$-$C_3$haloalkynyl, $C_1$-$C_3$haloalkoxy, $C_1$-$C_3$alkylthio, $C_1$-$C_3$haloalkylthio, allyloxy, propargyloxy, allylthio, propargylthio, haloallyloxy, haloallylthio, cyano and nitro, and from one to four substituents being selected from the group consisting of $C_1$-$C_3$alkyl, $C_1$-$C_3$alkoxy and halogen, and =X is =N—$NO_2$, =CH—$NO_2$, =N—CN or =CH—CO—$CF_3$, in free form or in the form of acid addition salts, can be used as agrochemical active ingredients and can be prepared in a manner known per se.

13 Claims, No Drawings

PYRIDINE COMPOUNDS WHICH ARE USEFUL AS PESTICIDES

The present invention relates to novel derivatives of amidines, to processes for their preparation, to pesticidal compositions that comprise those compounds, and to their use in the control of pests.

The amidine derivatives according to the invention correspond to formula

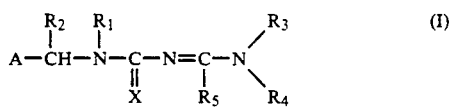

wherein $R_1$ is hydrogen, $C_1$-$C_4$alkyl or $C_3$-$C_6$cycloalkyl, $R_2$ is hydrogen or $C_1$-$C_4$alkyl, $R_3$ is hydrogen, $C_1$-$C_4$alkyl or $C_3$-$C_6$cycloalkyl and $R_4$ is $C_1$-$C_4$alkyl, $C_3$-$C_6$cycloalkyl or —$CH_2CH_2COOR_7$, or $R_3$ and $R_4$ together are —$(CH_2)_4$— or —$(CH_2)_5$—, $R_5$ is hydrogen, $C_1$-$C_4$alkyl,

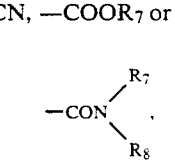

—$CH_2OCH_3$, —CN, —$COOR_7$ or

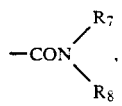

$R_6$ is hydrogen, chlorine, methyl or nitro, $R_7$ and $R_8$ are each methyl or ethyl, A is an unsubstituted or mono- to tetra-substituted, aromatic or non-aromatic, monocyclic or bicyclic, heterocyclic radical, one or two substituents being selected from the group consisting of $C_1$-$C_3$haloalkyl, cyclopropyl, halocyclopropyl, $C_2$-$C_3$alkenyl, $C_2$-$C_3$alkynyl, $C_2$-$C_3$haloalkenyl, $C_2$-$C_3$haloalkynyl, $C_1$-$C_3$haloalkoxy, $C_1$-$C_3$alkylthio, $C_1$-$C_3$haloalkylthio, allyloxy, propargyloxy, allylthio, propargylthio, haloallyloxy, haloallylthio, cyano and nitro, and from one to four substituents being selected from the group consisting of $C_1$-$C_3$alkyl, $C_1$-$C_3$alkoxy and halogen, and =X is =N—$NO_2$, =CH—$NO_2$, =N—CN or =CH—CO—$CF_3$.

Insecticidally active heterocyclic compounds having various additional structural features are known in the literature. EP-A 0 375 907 describes mono-unsaturated insecticidal active substances of formula

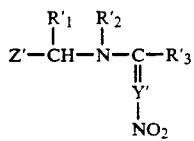

wherein Y' is CH or N, Z' is an unsubstituted or $C_1$-$C_4$alkyl- or halo-substituted heterocyclic radical, $R'_1$ and $R'_2$ are each hydrogen or $C_1$-$C_4$alkyl, $R'_3$ is —$SR'_4$ or

$R'_4$ is $C_1$-$C_4$alkyl and $R'_5$ and $R'_6$ are each hydrogen or $C_1$-$C_4$alkyl.

EP-A 0 383 091 describes analogous compounds having insecticidal activity, in which the meanings of the radicals Z' and $R'_1$ to $R'_6$ are broader and generalised.

The guanidine derivatives of formula

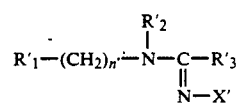

described in EP-A 0 376 279, wherein $R'_1$ is an unsubstituted or substituted heterocyclic radical, n' is 0 or 1, $R'_2$ is hydrogen or an unsubstituted or substituted hydrocarbon radical, $R'_3$ is an amino group and X' is cyano, are likewise insecticidally active.

In contrast to the above-mentioned structures known in the literature, the compounds I according to the invention have an amino-substituted alkylidene radical at one of the nitrogen atoms of the guanidine or enamine basic structure.

Finally, the α-unsaturated amines of formula

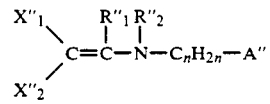

described in EP-A 0 302 389 have insecticidal-acaricidal activity, A" in the above formula being defined as a heterocyclic radical or a cyclic hydrocarbon radical, $R''_1$ being defined as a "group bonded via a nitrogen atom", $R''_2$ being defined as hydrogen or "a group bonded via a carbon, nitrogen or oxygen atom", one of the radicals $X''_1$ and $X''_2$ being defined as an electron-attracting group, the other radical $X''_1$ or $X''_2$ being defined as hydrogen or an electron-attracting group, and n being defined as 0, 1 or 2. However, compounds having an amidine structure, as have the compounds I according to the invention, are not described in EP-A 0 302 389.

The biological properties of the compounds described in the above-mentioned patent applications are not completely satisfactory in the field of pest control, and there is therefore a need to provide further compounds having pesticidal properties, that problem being solved according to the invention by the provision of the present compounds I.

The compounds I according to the invention also include acid addition salts, especially agrochemically acceptable acid addition salts. Examples of suitable (inorganic or organic) acids are hydrochloric acid, hydrobromic acid, sulfuric acid, phosphoric acid, nitric acid, acids having the same central atom and a higher or lower oxidation number, such as perchloric acid, nitrous acid or phosphorous acid, acetic acid and succinic acid.

The ring systems included in the definition of the heterocyclic radical A contain at least one hetero atom as a ring member; at least one of the atoms forming the basic cyclic structure is therefore other than carbon. In principle, those atoms of the periodic system of the elements that are able to form at least two covalent bonds are capable of acting as ring members that are other than carbon. The heterocyclic radical A is preferably unsaturated and bonded via a carbon ring member to the carbon atom in formula I that carries the radical $R_2$. Unsaturated ring systems A contain one or more double bonds; such ring systems A are preferably polyunsaturated and are generally of an aromatic nature. Such ring systems A that contain at least one nitrogen atom are preferred. Such rings A usually contain from one to three hetero atoms from the group consisting of oxygen, sulfur and nitrogen, not more than one of the hetero atoms in each case being an oxygen or a sulfur atom. Preferred are ring systems A that contain from one to three hetero atoms from the group consisting of oxygen, sulfur and nitrogen, A always containing at least one nitrogen atom and not more than one of the other hetero atoms which A may contain being an oxygen atom or a sulfur atom. Examples of heterocyclic radicals A according to the invention are found especially in the group consisting of the basic structures

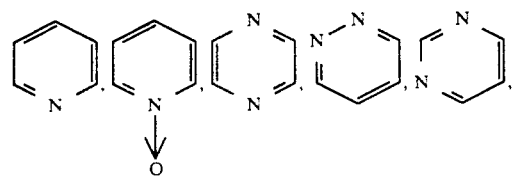

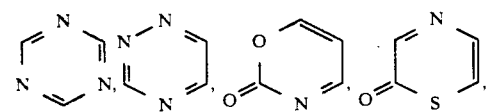

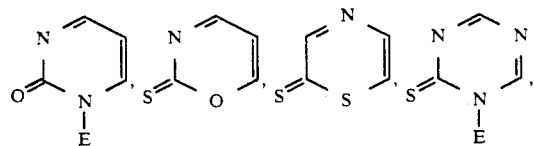

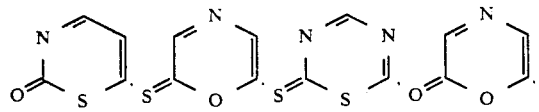

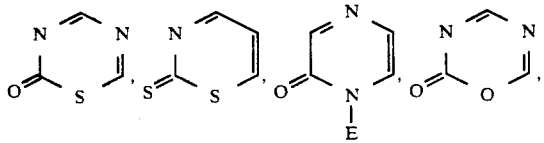

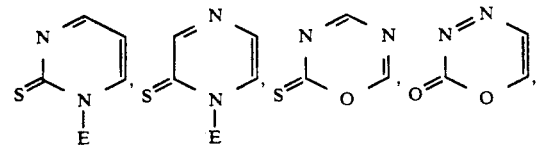

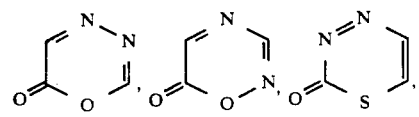

-continued

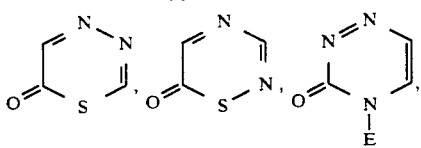

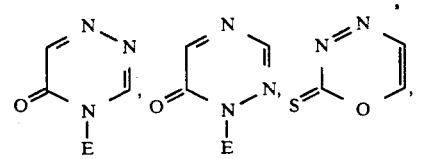

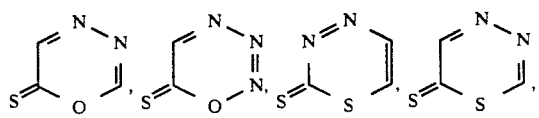

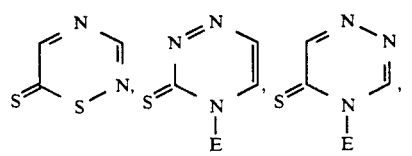

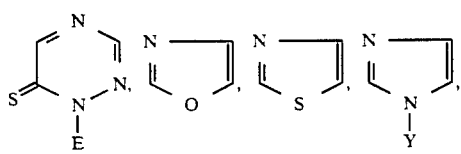

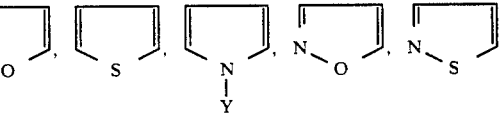

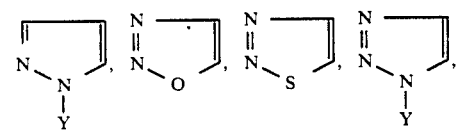

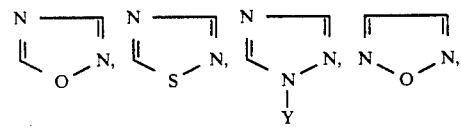

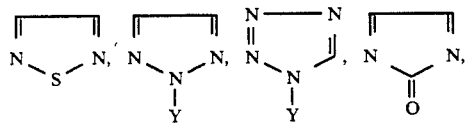

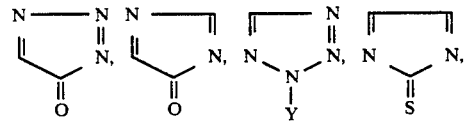

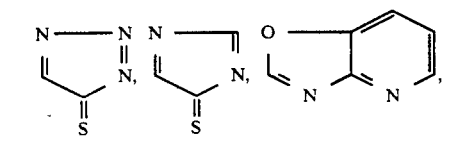

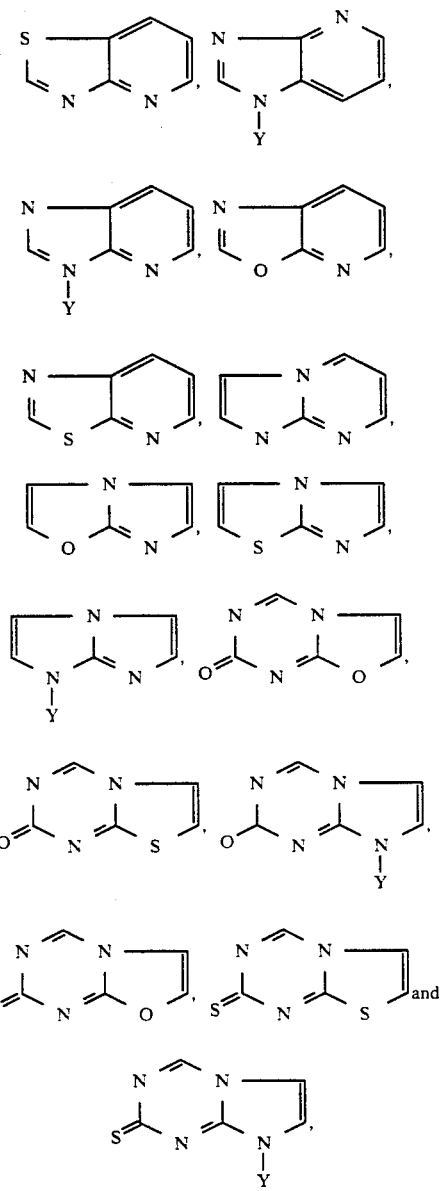

which basic structures are unsubstituted or, depending upon the number of substituents possible in the ring system, carry up to four of the substituents defined in claim 1, wherein E is $C_1$-$C_3$alkyl and Y is hydrogen, $C_1$-$C_3$alkyl or cyclopropyl, and are bonded via a carbon atom of the heterocyclic radical to the carbon atom in formula I that carries the radical $R_2$.

The heterocyclic radicals A are preferably unsubstituted or they carry one or two substituents selected from the group consisting of halogen, $C_1$-$C_3$alkyl, $C_1$-$C_3$haloalkyl, $C_1$-$C_3$haloalkoxy and $C_1$-$C_3$alkoxy. Especially preferred groups A are derived from pyridine and thiazole, such as pyrid-3-yl, 2-halopyrid-5-yl, 2,3-dihalopyrid-5-yl, 2-halo-1-oxido-5-pyridinio and 2-halothiazol-5-yl, especially 2-chloropyrid-5-yl.

Preferred compounds I are those wherein =X is =N—NO₂, =N—CN or =CH—NO₂.

Of those compounds I, special mention is to be made of those wherein $R_1$ is hydrogen, $C_1$-$C_3$alkyl or cyclopropyl, $R_2$ is hydrogen or methyl $R_3$ is $C_1$-$C_3$alkyl and $R_4$ is $C_1$-$C_3$alkyl or ethoxycarbonylethyl, or $R_3$ and $R_4$ together are —(CH₂)₄— or —(CH₂)₅—, and $R_5$ is hydrogen, methyl, ethyl, phenyl, —CH₂OCH₃, —CN, —COOC₂H₅ or

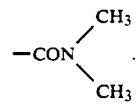

Of the latter, those compounds wherein $R_1$ is methyl, ethyl or cyclopropyl, $R_2$ is hydrogen, $R_3$ is methyl, $R_4$ is methyl and $R_5$ is hydrogen or methyl are preferred. Of those compounds, special preference is given to those wherein =X is =N—NO₂ or =CH—NO₂, especially those wherein =X is =N—NO₂.

There may be mentioned as preferred individual compounds of formula I:

(a) N-(2-chloropyrid-5-ylmethyl)-N-methyl-N'-(N,N-dimethylaminomethylene)-N''-nitroguanidine,
(b) N-(2-chloropyrid-5-ylmethyl)-N-methyl-N'-[1-(N,N-dimethylamino)ethylidene]-N''-nitroguanidine,
(c) N-pyrid-3-ylmethyl-N-methyl-N'-(N,N-dimethylaminomethylene)-N''-nitroguanidine,
(d) N-(2-chloropyrid-5-ylmethyl)-N-methyl-N'-(N,N-dimethylaminomethylene)-N''-cyanoguanidine,
(e) 1-[N-(2-chloropyrid-5-ylmethyl)-N-methylamino]-1-(N,N-dimethylaminomethyleneamino)-2-nitroethene,
(f) 1-[N-(2-chloropyrid-5-ylmethyl)-N-ethylamino]-1-(N,N-dimethylaminomethyleneamino)-2-nitroethene,
(g) 1-[N-(2-chloropyrid-5-ylmethyl)-N-cyclopropylamino]-1-(N,N-dimethylaminomethyleneamino)-2-nitroethene,
(h) 1-[N-(2-chlorothiazol-5-ylmethyl)-N-methylamino]-1-(N,N-dimethylaminomethyleneamino)-2-nitroethene,
(i) 1-[N-(2-chlorothiazol-5-ylmethyl)-N-ethylamino]-1-(N,N-dimethylaminomethyleneamino)-2-nitroethene,
(j) 1-[N-(2-chlorothiazol-5-ylmethyl)-N-cyclopropylamino]-1-(N,N-dimethylaminomethyleneamino)-2-nitroethene,
(k) 1-[N-(2-chloro-1-oxido-5-pyridiniomethyl)-N-methylamino]-1-(N,N-dimethylaminomethyleneamino)-2-nitroethene,
(l) 1-[N-(2-chloro-1-oxido-5-pyridiniomethyl)-N-ethylamino]-1-(N,N-dimethylaminomethyleneamino)-2-nitroethene,
(m) 1-[N-(2-chloro-1-oxido-5-pyridiniomethyl)-N-cyclopropylamino]-1-(N,N-dimethylaminomethyleneamino)-2-nitroethene,
(n) N-(2-chlorothiazol-5-ylmethyl)-N-methyl-N'-(N,N-dimethylaminomethylene)-N''-nitroguanidine,
(o) N-(2-chlorothiazol-5-ylmethyl)-N-ethyl-N'-(N,N-dimethylaminomethylene)-N''-nitroguanidine,
(p) N-(2-chlorothiazol-5-ylmethyl)-N-cyclopropyl-N'-(N,N-dimethylaminomethylene)-N''-nitroguanidine,
(q) N-(2-chloropyrid-5-ylmethyl)-N-ethyl-N'-(N,N-dimethylaminomethylene)-N''-nitroguanidine and
(r) N-(2-chloropyrid-5-ylmethyl)-N-cyclopropyl-N'-(N,N-dimethylaminomethylene)-N''-nitroguanidine.

In the definition of formula I according to the invention, the individual generic terms are to be understood as having the following meanings:

The halogen atoms that come into consideration as substituents are fluorine and chlorine as well as bromine and iodine, with fluorine, chlorine and bromine being preferred. Halogen is here to be understood as being an independent substituent or a part of a substituent, such as in haloalkyl, haloalkylthio, haloalkoxy, halocyclopropyl, haloalkenyl, haloalkynyl, haloallyloxy or haloallylthio. The (halo)alkyl, (halo)alkylthio, (halo)alkenyl, (halo)alkynyl and (halo)alkoxy radicals that come into consideration as substituents may be straight-chained or branched. There may be mentioned as examples of such alkyl radicals methyl, ethyl, propyl, isopropyl, butyl, isobutyl, sec-butyl and tert-butyl. Suitable alkoxy radicals that may be mentioned are: methoxy, ethoxy, propoxy and isopropoxy. Alkylthio is methylthio, ethylthio, isopropylthio or propylthio. Halo-substituted groups, such as haloalkyl, may be partially halogenated or perhalogenated. Examples of the alkyl elements of those halo-substituted groups are methyl substituted from one to three times by fluorine, chlorine and/or bromine, such as $CHF_2$ or $CF_3$; ethyl substituted from one to five times by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl substituted from one to seven times by fluorine, chlorine and/or bromine, such as $CH_2CHBrCH_2Br$, $CF_2CHFCF_3$, $CH_2CF_2CF_3$ or $CH(CF_3)_2$; butyl or one of its isomers substituted from one to nine times by fluorine, chlorine and/or bromine, such as $CF(CF_3)CHFCF_3$ or $CH_2(CF_2)_2CF_3$. There may also be mentioned by way of example: 2-chlorocyclopropyl, 2,2-difluorocyclopropyl, 2,2-difluorovinyl, 2,2-dichlorovinyl, 2-chloroallyl, 2,3-dichloroallyl and 2,3-dibromoallyl.

Cycloalkyl radicals are cyclopropyl, cyclobutyl, cyclopentyl and cyclohexyl. Alkenyl and alkynyl groups contain an unsaturated carbon-carbon bond. Typical examples are allyl and propargyl, and also vinyl and ethynyl.

The compounds of formula I according to the invention can be prepared analogously to known processes, for example by a) reacting a compound of formula

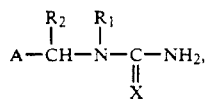    (II)

wherein $R_1$, $R_2$, A and X are as defined for formula I, in an inert aprotic solvent with a compound of formula

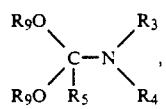    (III)

wherein $R_3$, $R_4$ and $R_5$ are as defined for formula I and $R_9$ is $C_1$-$C_4$alkyl, or b) reacting a compound of formula

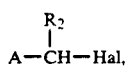    (IV)

wherein $R_2$ and A are as defined for formula I and Hal is chlorine, bromine or iodine, with a compound of formula

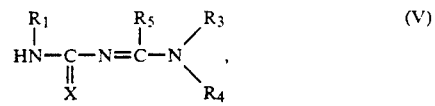    (V)

wherein $R_1$, $R_3$, $R_4$, $R_5$ and X are as defined for formula I, in the presence of an acid acceptor, in a solvent, at from $-20°$ to $+120°$ C., and in each case isolating the resulting compound of formula I or converting it into an acid addition salt and isolating the salt.

According to a preferred form of process variant a), the reaction is carried out in an inert aprotic solvent, such as a hydrocarbon, a chlorinated hydrocarbon, an ether, a nitrile or an amide, at from 20° to 150° C. under atmospheric pressure. It is especially preferred to carry out the reaction at from 50° to 120° C. in tetrahydrofuran, dioxane or toluene as solvent.

A preferred form of process variant b) comprises carrying out the reaction in the presence of sodium hydride, sodium amide, potassium carbonate, triethylamine or diethylaniline as acid acceptor and in N,N-dimethylformamide, 1-methylpyrrolidone, dimethyl sulfoxide, sulfolane, tetrahydrofuran or acetonitrile as solvent. It is especially preferred to carry out the reaction at from $-10°$ to $+30°$ C. using hydride or sodium amide as acid acceptor.

The compounds of formulae II, III, IV and V are known or can be prepared analogously to known processes. The compounds of formula V are novel, and the invention relates also to them; they can be prepared analogously to known processes, for example as described in the Preparation Examples or according to analogous methods. Preference is given to those compounds V wherein the variables have the same meanings as in the preferred compounds I.

The compounds I according to the invention are valuable active ingredients in pest control while being well tolerated by warm-blooded animals, fish and plants. The compounds according to the invention are effective especially against insects and arachnids which occur on useful plants and ornamentals in agriculture and horticulture, especially in rice, cotton, vegetable and fruit crops, and in forestry. The compounds according to the invention can also be used in the protection of stored goods and material stocks and in the hygiene sector, especially the protection of domestic animals and productive livestock. The compounds I are effective against all or individual development stages of normally sensitive and also resistant species of pest. Their action may manifest itself, for example, in the death of the pests, which occurs immediately or not until some time later, for example during moulting, or in reduced oviposition and/or a reduced hatching rate.

The above-mentioned pests include:
of the order Lepidoptera, for example

Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia lycopersicella, Leucoptera scitella*, Lithocollethis spp., *Lobesia botrana*, Lymantria spp., Lyonetia spp., Malacosoma spp., *Mamestra brassicae, Manduca sexta*, Operophtera spp., *Ostrinia nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp., Sesamia spp., Sparganothis spp., Spodoptera spp., Synathedon spp., Thaumetopoea spp., Tortrix spp., Trichoplusia ni and Yponomeuta spp.;

of the order Coleoptera, for example

Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

of the order Orthoptera, for example

Blatta spp., Blattella spp., Gryllotalpa spp., *Leucophaea maderae*, Locusta spp., Periplaneta spp. and Schistocerca spp.;

of the order Isoptera, for example

Reticulitermes spp.;

of the order Psocoptera, for example

Liposcelis spp.;

of the order Anoplura, for example

Haematopinus spp., Linognathus spp., Pediculus spp., Pemphigus spp. and Phylloxera spp.;

of the order Mallophaga, for example

Damalinea spp. and Trichodectes spp.;

of the order Thysanoptera, for example

Frankliniella spp., Hercinothrips spp., Taeniothrips spp., *Thrips palmi, Thrips tabaci* and *Scirtothrips aurantii;* of the order Heteroptera, for example

Cimex spp., *Distantiella theobroma*, Dysdercus spp., Euchistus spp., Eurygaster spp., Leptocorisa spp., Nezara spp., Piesma spp., Rhodnius spp., *Sahlbergella singularis*, Scotinophara spp. and Triatoma spp.;

of the order Homoptera, for example

*Aleurothrixus floccosus, Aleyrodes brassicae*, Aonidiella spp., Aphididae, Aphis spp., Aspidiotus spp., *Bemisia tabaci*, Ceroplaster spp., *Chrysomphalus aonidium, Chrysomphalus dictyospermi, Coccus hesperidum*, Empoasca spp., *Eriosoma larigerum*, Erythroneura spp., Gascardia spp., Laodelphax spp., *Lecanium corni*, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica*, Quadraspidiotus spp., Rhopalosiphum spp., Saissetia spp., Scaphoideus spp., Schizaphis spp., Sitobion spp., *Trialeurodes vaporariorum, Trioza erytreae* and Unaspis citri;

of the order Hymenoptera, for example

Acromyrmex, Atta spp., Cephus spp., Diprion spp., Diprionidae, *Gilpinia polytoma*, Hoplocampa spp., Lasius spp., *Monomorium pharaonis*, Neodiprion spp., Solenopsis spp. and Vespa spp.;

of the order Diptera, for example

Aedes spp., *Antherigona soccata, Bibio hortulanus, Calliphora erythrocephala*, Ceratitis spp., Chrysomyia spp., Culex spp., Cuterebra spp., Dacus spp., *Drosophila melanogaster*, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., *Oscinella frit, Pegomyia hyoscyami*, Phorbia spp., *Rhagoletis pomonella*, Sciara spp., Stomoxys spp., Tabanus spp., Tannia spp. and Tipula spp.;

of the order Siphonaptera, for example

Ceratophyllus spp. and Xenopsylla cheopis and of the order Thysanura, for example

*Lepisma saccharina.*

The good pesticidal activity of the compounds I according to the invention corresponds to a mortality of at least 50–60% of the mentioned pests.

The activity of the compounds of the invention and of the compositions comprising them can be substantially broadened and adapted to prevailing circumstances by the addition of other insecticides. Examples of suitable additives include representative of the following classes of compounds: organophosphorus compounds, nitrophenols and derivatives thereof, formamidines, ureas, carbamates, pyrethroids, chlorinated hydrocarbons, and Bacillus thuringiensis preparations.

The compounds I are used in unmodified form or, preferably, together with the adjuvants conventionally employed in formulation technology, and can therefore be formulated in known manner e.g. into emulsifiable concentrates, directly sprayable or dilutable solutions, dilute emulsions, wettable powders, soluble powders, dusts, granules, and also encapsulations in polymer substances. As with the nature of the compositions, the methods of application, such as spraying, atomising, dusting, scattering or pouring, are chosen in accordance with the intended objectives and the prevailing circumstances. The compounds i are also suitable for use in the treatment of seeds. It is possible both to treat or dress the seeds with the active ingredient or with a formulation comprising the active ingredient before sowing, and to apply the active ingredient to the furrow at the time of sowing.

The formulations, i.e. the compositions, preparations or mixtures comprising the compound (active ingredient) of formula I, or a combination of that compound with other insecticides, and, where appropriate, solid or liquid adjuvants, are prepared in known manner, e.g. by homogeneously mixing and/or grinding the active ingredient with extenders, e.g. solvents, solid carriers and, where appropriate, surface-active compounds (surfactants).

Suitable solvents are: aromatic hydrocarbons, preferably the $C_8$ to $C_{12}$ fractions of alkylbenzenes, such as xylene mixtures or alkylated naphthalenes, aliphatic or cycloaliphatic hydrocarbons, such as cyclohexane, paraffins or tetrahydronaphthalene, alcohols such as ethanol, propanol or butanol, glycols and their ethers and esters, such as propylene glycol, dipropylene glycol ether, ethylene glycol, ethylene glycol monomethyl or monoethyl ether, ketones, such as cyclohexanone, isophorone or diacetone alcohol, strongly polar solvents, such as N-methyl-2-pyrrolidone, dimethyl sulfoxide or N,N-dimethylformamide, water, and also vegetable oils such as rape oil, castor oil, coconut oil or soybean oil; and, where appropriate, also silicone oils.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable non-sorbent carriers are calcite or sand. In addition, a great number of granulated materials of inorganic or organic nature can be used, especially dolomite or pulverised plant residues. Depending on the nature of the compound of formula I to be formulated, or of the combination of that compound with other insecticides, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tall oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates. The fatty sulfonates or sulfates are usually in the form of alkali metal salts, alkaline earth metal salts or unsubstituted or substituted ammonium salts and generally contain a $C_8$–$C_{22}$alkyl radical, which also includes the alkyl moiety of acyl radicals; there may be mentioned by way of example the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing approximately 8 to 22 carbon atoms. Examples of alkylarylsulfonates are the sodium, calcium or triethanolammonium salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology are described, for example, in the following publications:

"McCutcheon's Detergents and Emulsifiers Annual", MC Publishing Corp., Glen Rock, NJ, USA, 1988, H. Stache, "Tensid-Taschenbuch", 2nd edition, C. Hanser Verlag, Munich, Vienna 1981, and M. and J. Ash, "Encyclopedia of Surfactants", Vol. I-III, Chemical Publishing Co., New York, 1980-1981.

The pesticidal compositions usually comprise 0.1 to 99%, preferably 0.1 to 95%, of a compound of formula I or a combination of that compound with other insecticides, 1 to 99.9% of a solid or liquid adjuvant, and 0 to 25%, preferably 0.1 to 25%, of a surfactant. Whereas commercial products will preferably be formulated as concentrates, the end user will normally employ dilute formulations which have considerably lower active ingredient concentrations. Typical application concentrations are from 0.1 to 1000 ppm, preferably from 0.1 to 500 ppm. The rates of application per hectare are generally from 1 to 1000 g of active ingredient per hectare, preferably from 25 to 500 g/ha.

Preferred formulations have especially the following composition (throughout, percentages are by weight):

| Emulsifiable concentrates: | |
|---|---|
| active ingredient: | 1 to 90%, preferably 5 to 20% |
| surface-active agent: | 1 to 30%, preferably 10 to 20% |
| liquid carrier: | 5 to 94%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.5 to 30%, preferably 3 to 15% |
| solid carrier: | 99.5 to 70%, preferably 97 to 85% |

The compositions may also comprise further auxiliaries, such as stabilizers, for example vegetable oils or epoxidised vegetable oils (e.g. epoxidised coconut oil, rape oil or soybean oil), antifoams, for example silicone oil, preservatives, viscosity regulators, binders, tackifiers as well as fertilisers or other active ingredients for obtaining special effects.

The following Examples serve to illustrate the invention, but do not limit the invention. Temperatures are given in degrees Celsius.

PREPARATION EXAMPLES

EXAMPLE 1

N-(2-Chloropyrid-5-ylmethyl)-N-methyl-N'-(N,N-dimethylaminomethylene)-N''-nitroguanidine (Table 1, compound no. 1.001).

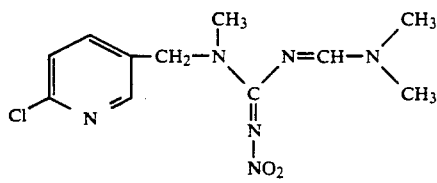

Variant a): 1.5 g of N,N-dimethylformamide-diethylacetal are added to 2.43 g of N-(2-chloropyrid-5-ylmethyl)-N-methyl-N'-nitroguanidine in 75 ml of dioxane. The mixture is heated at 130° C. for 45 minutes and is then freed of solvent using a rotary evaporator. The crude product is chromatographed over silica gel using first ethyl acetate and then ethyl acetate/ethanol (5:1). A viscous oil is formed which, after the addition of hexane, yields crystals of the desired product (m.p.: 85°-89° C.).

Variant b): 0.6 g of sodium hydride (80%, in mineral oil) is added in small portions, under a nitrogen atmosphere, to 3.46 g of N-(N,N-dimethylaminomethylene)-N'-methyl-N''-nitroguanidine in 35 ml of absolute N,N-dimethylformamide. The reaction mixture is stirred for one hour at 5° C. and then a solution of 3.24 g of 2-chloro-5-chloromethylpyridine in 10 ml of N,N-dimethylformamide is added dropwise and the reaction mixture is stirred overnight at 20° C. After filtering, the filtrate is concentrated under a high vacuum and the resulting oil is purified by column chromatography (SiO₂/ethyl acetate). The desired product is a white powder (m.p.: 90°-94° C.).

EXAMPLE 2

1-[N-(2-Chloropyrid-5-ylmethyl)-N-methylamino]-1-(N,N-dimethylaminomethyleneamino)-2-nitroethene (Table 5, compound no. 5.001).

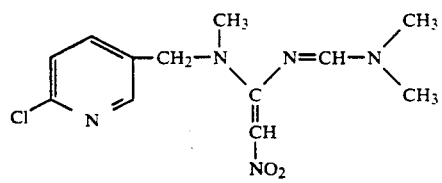

Variant a): A mixture of 0.9 g of 1-amino-1-[N-(2-chloropyrid-5-ylmethyl)-N-methylamino]-2-nitroethene, 0.68 ml of N,N-dimethylformamide-diethylacetal and 20 ml of 1,3-dioxane is heated under reflux for 10 hours under an argon atmosphere. After removal of the solvent by distillation, diethyl ether is added to the residue and the crystalline product is filtered off (m.p.: 108°-110° C.).

Variant b1): 2.01 g of potassium carbonate are added to a mixture of 1.0 g of 1-(N,N-dimethylaminomethyleneamino)-1-(N-methylamino)-2-nitroethene, 1.13 g of 2-chloro-5-chloromethylpyridine and 10 ml of N,N-dimethylformamide. The reaction mixture is then stirred at 50° C. for 2 days. After filtering, the filtrate is concentrated under a high vacuum and the resulting crude product is purified by column chromatography [SiO₂; CH₂Cl₂/MeOH (10:1)], yielding the desired product, which melts at 107°-110° C.

Variant b2): 0.19 g of sodium hydride (80%, in mineral oil) is added to a suspension of 1.0 g of 1-(N,N-dimethylaminomethyleneamino)-1-(N-methylamino)-2-nitroethene in 20 ml of N,N-dimethylformamide. After stirring at room temperature for six hours, 1.13 g of 2-chloro-5-chloromethylpyridine are added. The reaction mixture is then stirred overnight at room temperature. After filtering, the filtrate is concentrated under a high vacuum and the resulting crude product is purified by column chromatography [SiO₂; CH₂Cl₂/MeOH (10:1)], yielding the desired product, which melts at 108°-110° C.

EXAMPLE 3

N-Cyclopropyl-N'-(N,N-dimethylaminomethylene)-N''-nitroguanidine (Preparation Example for compounds of formula V).

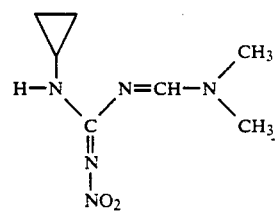

a) 140 g of S-methylisothiourea sulfate are added in portions at −10° C., within a period of one hour, to a mixture of 140 ml of fuming nitric acid and 420 ml of concentrated sulfuric acid. After the reaction mixture has been stirred at 0° C. for one hour to complete the reaction, it is poured onto 2 liters of ice/water and the white product is filtered off with suction. The filter cake is washed with 250 ml of water, 100 ml of cold ethanol and 150 ml of diethyl ether and dried at room temperature in vacuo, yielding S-methyl-N-nitroisothiourea (m.p.: 162°-164° C.).

b) 27 g of S-methyl-N-nitroisothiourea are heated under reflux for 3.5 hours in admixture with 12.6 g of cyclopropylamine and 15 ml of ethanol. The reaction mixture is then cooled to −5° C. and the product is filtered off and washed with a small amount of cold ethanol and diethyl ether, yielding N-cyclopropyl-N'-nitroguanidine (m.p.: 127°-130° C.).

c) 14.4 g of N-cyclopropyl-N'-nitroguanidine are added to 14.7 g of N,N-dimethylformamide-diethylacetal. After stirring at 70°-75° C. for 1.5 hours, the mixture is cooled and concentrated using a rotary evaporator. The crude product is stirred into diethyl ether, filtered off and washed with further diethyl ether, yielding N-cyclopropyl-N'-(N,N-dimethylaminomethylene)-N''-nitroguanidine (m.p.: 120°-122° C.).

The following can be prepared analogously:
N-ethyl-N'-(N,N-dimethylaminomethylene)-N''-nitroguanidine (m.p.: 93°-96° C.),
N-(N,N-dimethylaminomethylene)-N'-methyl-N''-nitroguanidine (m.p.: 141°-143° C.),
N-cyclopropyl-N'-[1-(N,N-dimethylamino)ethylidene]-N''-nitroguanidine (m.p.: 92°-94° C.) and
N-ethyl-N'-[1-(N,N-dimethylamino)ethylidene]-N''-nitroguanidine (m.p.: 74°-77° C.).

EXAMPLE 4

1-(N,N-Dimethylaminomethyleneamino)-1-(N-methylamino)-2-nitroethene (Preparation Example for compounds of formula V).

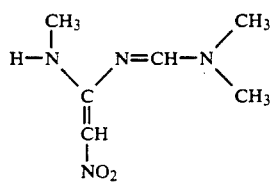

32.2 ml of N,N-dimethylformamide-diethyl-acetal are added to 20 g of 1-amino-1-(N-methylamino)-2-nitroethene in 100 ml of dioxane. The reaction mixture is heated at 50° C. for 16 hours. The resulting crystals are filtered off and washed with diethyl ether, yielding the desired product, which melts at 219° C.

The following can be prepared analogously:
1-(N-ethylamino)-1-(N,N-dimethylaminomethyleneamino)-2-nitroethene (starting from 1-(N-ethylamino)-1-amino-2-nitroethene) and
1-(N-cyclopropylamino)-1-(N,N-dimethylaminomethyleneamino)-2-nitroethene (starting from 1-amino-1-(N-cyclopropylamino)-2-nitroethene).

In a manner analogous to that described in Examples 1 to 4 it is also possible to prepare the other compounds of formula I listed in Tables 1 to 13 below. In the column headed "m.p." in those Tables, the temperatures indicated denote the melting point of the compound in question. Where appropriate, other physical data are also listed in that column "m.p."; $n_D^T$, for example, denotes the refractive index of the compound in question at temperature T° C.

TABLE 1

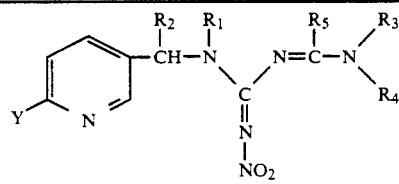

| Comp. No. | Y | $R_1$ | $R_2$ | $R_3$ | $R_4$ | $R_5$ | m.p. |
|---|---|---|---|---|---|---|---|
| 1.001 | Cl | $CH_3$ | H | $CH_3$ | $CH_3$ | H | 85–89° C. |
| 1.002 | Cl | H | H | $CH_3$ | $CH_3$ | H | 142–143° C. |
| 1.003 | Cl | $CH_3$ | H | $CH_3$ | $CH_3$ | $CH_3$ | 72–76° C. |
| 1.004 | Cl | $CH_3$ | H | $CH_3$ | $C_2H_5$ | H | |
| 1.005 | Cl | $CH_3$ | H | $C_2H_5$ | $C_2H_5$ | H | |
| 1.006 | Cl | $CH_3$ | H | $nC_3H_7$ | $nC_3H_7$ | H | |
| 1.007 | Cl | $CH_3$ | H | $C_2H_5$ | $CH_3$ | $CH_3$ | |
| 1.008 | Cl | H | H | $CH_3$ | $CH_3$ | $CH_3$ | |
| 1.009 | Cl | $CH_3$ | H | $C_2H_5$ | $C_2H_5$ | $CH_3$ | |
| 1.010 | Cl | $CH_3$ | $CH_3$ | $CH_3$ | $CH_3$ | H | |
| 1.011 | Cl | $CH_3$ | $CH_3$ | $C_2H_5$ | $C_2H_5$ | H | |
| 1.012 | Cl | $C_2H_5$ | H | $CH_3$ | $CH_3$ | H | 81–84° C. |
| 1.013 | Cl | $C_2H_5$ | H | $CH_3$ | $CH_3$ | $CH_3$ | 113–116° C. |
| 1.014 | Cl | $C_2H_5$ | H | $CH_3$ | $C_2H_5$ | H | |
| 1.015 | Cl | $C_2H_5$ | H | $C_2H_5$ | $C_2H_5$ | H | |
| 1.016 | Cl | $C_2H_5$ | H | $nC_3H_7$ | $nC_3H_7$ | H | |
| 1.017 | Cl | $C_2H_5$ | H | $CH_3$ | $CH_3$ | $C_2H_5$ | |
| 1.018 | Cl | $C_2H_5$ | H | $C_2H_5$ | $CH_3$ | $CH_3$ | |
| 1.019 | Cl | $C_2H_5$ | H | $C_2H_5$ | $C_2H_5$ | $CH_3$ | |
| 1.020 | Cl | $C_2H_5$ | $CH_3$ | $CH_3$ | $CH_3$ | H | |
| 1.021 | Cl | $C_2H_5$ | $CH_3$ | $C_2H_5$ | $C_2H_5$ | H | resin |
| 1.022 | Cl | ▷– | H | $CH_3$ | $CH_3$ | H | resin |
| 1.023 | Cl | ▷– | H | $CH_3$ | $CH_3$ | $CH_3$ | |
| 1.024 | Cl | ▷– | H | $CH_3$ | $C_2H_5$ | H | |
| 1.025 | Cl | ▷– | H | $C_2H_5$ | $C_2H_5$ | H | |
| 1.026 | Cl | ▷– | H | $nC_3H_7$ | $nC_3H_7$ | H | |
| 1.027 | Cl | ▷– | H | $CH_3$ | $CH_3$ | $C_2H_5$ | |

TABLE 1-continued

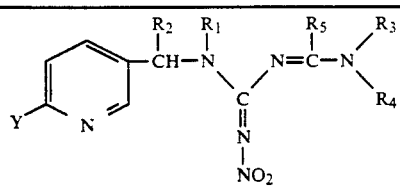

| Comp. No. | Y | $R_1$ | $R_2$ | $R_3$ | $R_4$ | $R_5$ | m.p. |
|---|---|---|---|---|---|---|---|
| 1.028 | Cl | ▷ | H | $C_2H_5$ | $CH_3$ | $CH_3$ | |
| 1.029 | Cl | ▷ | H | $C_2H_5$ | $C_2H_5$ | $CH_3$ | |
| 1.030 | Cl | ▷ | $CH_3$ | $CH_3$ | $CH_3$ | H | |
| 1.031 | Cl | ▷ | $CH_3$ | $C_2H_5$ | $C_2H_5$ | H | |
| 1.032 | Cl | $nC_3H_7$ | H | $CH_3$ | $CH_3$ | H | |
| 1.033 | Cl | $nC_3H_7$ | H | $C_2H_5$ | $C_2H_5$ | H | |
| 1.034 | Cl | $CH_3$ | H | —$CH_2CH_2CH_2CH_2$— | | H | |
| 1.035 | Cl | $CH_3$ | H | —$CH_2CH_2CH_2CH_2CH_2$— | | H | |
| 1.036 | Cl | H | $CH_3$ | $CH_3$ | $CH_3$ | H | |
| 1.037 | Cl | H | $CH_3$ | $CH_3$ | $CH_3$ | $CH_3$ | |
| 1.038 | H | $CH_3$ | H | $CH_3$ | $CH_3$ | H | 51–54° C. |
| 1.039 | H | $CH_3$ | H | $CH_3$ | $CH_3$ | $CH_3$ | |
| 1.040 | H | $CH_3$ | H | $C_2H_5$ | $C_2H_5$ | H | |
| 1.041 | H | H | H | $CH_3$ | $CH_3$ | H | |
| 1.042 | H | $C_2H_5$ | H | $CH_3$ | $CH_3$ | H | |
| 1.043 | H | ▷ | H | $CH_3$ | $CH_3$ | H | |
| 1.044 | Cl | $CH_3$ | H | $CH_3$ | $CH_3$ | phenyl | |
| 1.045 | Cl | $CH_3$ | H | $CH_3$ | $CH_3$ | —$CH_2OCH_3$ | |
| 1.046 | Cl | $CH_3$ | H | $CH_3$ | $CH_3$ | —CN | |
| 1.047 | Cl | $CH_3$ | H | $CH_3$ | $CH_3$ | —$COOC_2H_5$ | |
| 1.048 | Cl | $CH_3$ | H | $CH_3$ | $CH_3$ | —$CON(CH_3)_2$ | |
| 1.049 | Cl | $CH_3$ | H | $CH_3$ | —$CH_2CH_2COOC_2H_5$ | H | |

TABLE 2

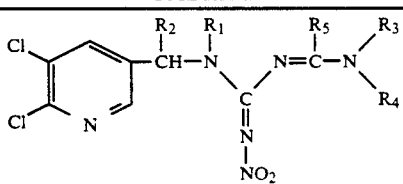

| Comp. No. | $R_1$ | $R_2$ | $R_3$ | $R_4$ | $R_5$ | m.p. |
|---|---|---|---|---|---|---|
| 2.001 | $CH_3$ | H | $CH_3$ | $CH_3$ | H | |
| 2.002 | H | H | $CH_3$ | $CH_3$ | H | |
| 2.003 | $CH_3$ | H | $CH_3$ | $CH_3$ | $CH_3$ | |
| 2.004 | $CH_3$ | H | $CH_3$ | $C_2H_5$ | H | |
| 2.005 | $CH_3$ | H | $C_2H_5$ | $C_2H_5$ | H | |
| 2.006 | $CH_3$ | H | $nC_3H_7$ | $nC_3H_7$ | H | |
| 2.007 | $CH_3$ | H | $C_2H_5$ | $CH_3$ | $CH_3$ | |

TABLE 2-continued

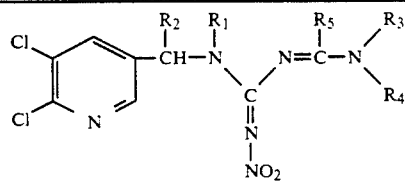

| Comp. No. | R₁ | R₂ | R₃ | R₄ | R₅ | m.p. |
|---|---|---|---|---|---|---|
| 2.008 | H | H | CH₃ | CH₃ | CH₃ | |
| 2.009 | CH₃ | H | C₂H₅ | C₂H₅ | CH₃ | |
| 2.010 | CH₃ | CH₃ | CH₃ | CH₃ | H | |
| 2.011 | CH₃ | CH₃ | C₂H₅ | C₂H₅ | H | |
| 2.012 | C₂H₅ | H | CH₃ | CH₃ | H | amorphous |
| 2.013 | C₂H₅ | H | CH₃ | CH₃ | CH₃ | |
| 2.014 | C₂H₅ | H | CH₃ | C₂H₅ | H | |
| 2.015 | C₂H₅ | H | C₂H₅ | C₂H₅ | H | |
| 2.016 | C₂H₅ | H | nC₃H₇ | nC₃H₇ | H | |
| 2.017 | C₂H₅ | H | CH₃ | CH₃ | C₂H₅ | |
| 2.018 | C₂H₅ | H | C₂H₅ | CH₃ | CH₃ | |
| 2.019 | C₂H₅ | H | C₂H₅ | C₂H₅ | CH₃ | |
| 2.020 | C₂H₅ | CH₃ | CH₃ | CH₃ | H | |
| 2.021 | C₂H₅ | CH₃ | C₂H₅ | C₂H₅ | H | |
| 2.022 | cyclopropyl | H | CH₃ | CH₃ | H | |
| 2.023 | cyclopropyl | H | CH₃ | CH₃ | CH₃ | |
| 2.024 | cyclopropyl | H | CH₃ | C₂H₅ | H | |
| 2.025 | cyclopropyl | H | C₂H₅ | C₂H₅ | H | |
| 2.026 | cyclopropyl | H | nC₃H₇ | nC₃H₇ | H | |
| 2.027 | cyclopropyl | H | CH₃ | CH₃ | C₂H₅ | |
| 2.028 | cyclopropyl | H | C₂H₅ | CH₃ | CH₃ | |
| 2.029 | cyclopropyl | H | C₂H₅ | C₂H₅ | CH₃ | |
| 2.030 | cyclopropyl | CH₃ | CH₃ | CH₃ | H | |
| 2.031 | cyclopropyl | CH₃ | C₂H₅ | C₂H₅ | H | |
| 2.032 | nC₃H₇ | H | CH₃ | CH₃ | H | |
| 2.033 | nC₃H₇ | H | C₂H₅ | C₂H₅ | H | |
| 2.034 | CH₃ | H | —CH₂CH₂CH₂CH₂— | | H | |
| 2.035 | CH₃ | H | —CH₂CH₂CH₂CH₂CH₂— | | H | |
| 2.036 | H | CH₃ | CH₃ | CH₃ | H | |
| 2.037 | H | CH₃ | CH₃ | CH₃ | CH₃ | |

TABLE 2-continued

| Comp. No. | R₁ | R₂ | R₃ | R₄ | R₅ | m.p. |
|---|---|---|---|---|---|---|
| 2.038 | $CH_3$ | H | $CH_3$ | $CH_3$ | phenyl | |
| 2.039 | $CH_3$ | H | $CH_3$ | $CH_3$ | $-CH_2OCH_3$ | |
| 2.040 | $CH_3$ | H | $CH_3$ | $CH_3$ | $-CN$ | |
| 2.041 | $CH_3$ | H | $CH_3$ | $CH_3$ | $-COOC_2H_5-$ | |
| 2.042 | $CH_3$ | H | $CH_3$ | $CH_3$ | $-CO-N(CH_3)_2$ | |
| 2.043 | $CH_3$ | H | $CH_3$ | $-CH_2CH_2COOC_2H_5$ | H | |

TABLE 3

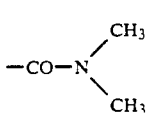

| Comp. No. | R₁ | R₄ | R₃ | R₅ | m.p. |
|---|---|---|---|---|---|
| 3.001 | $CH_3$ | $CH_3$ | $CH_3$ | H | 87–90° C. |
| 3.002 | H | $CH_3$ | $CH_3$ | H | |
| 3.003 | $CH_3$ | $CH_3$ | $CH_3$ | $CH_3$ | |
| 3.004 | $CH_3$ | $CH_3$ | $C_2H_5$ | H | |
| 3.005 | $CH_3$ | $C_2H_5$ | $C_2H_5$ | H | |
| 3.006 | $CH_3$ | $C_2H_5$ | $CH_3$ | $CH_3$ | |
| 3.007 | $CH_3$ | $C_2H_5$ | $C_2H_5$ | $CH_3$ | |
| 3.008 | $C_2H_5$ | $CH_3$ | $CH_3$ | H | amorphous |
| 3.009 | $C_2H_5$ | $CH_3$ | $CH_3$ | $CH_3$ | |
| 3.010 | $C_2H_5$ | $CH_3$ | $C_2H_5$ | H | |
| 3.011 | $C_2H_5$ | $C_2H_5$ | $C_2H_5$ | H | |
| 3.012 | $C_2H_5$ | $nC_3H_7$ | $nC_3H_7$ | H | |
| 3.013 | $C_2H_5$ | $CH_3$ | $CH_3$ | $C_2H_5$ | |
| 3.014 | $C_2H_5$ | $C_2H_5$ | $CH_3$ | $CH_3$ | |
| 3.015 | $C_2H_5$ | $C_2H_5$ | $C_2H_5$ | $CH_3$ | |
| 3.016 | cyclopropyl | $CH_3$ | $CH_3$ | H | oil |
| 3.017 | cyclopropyl | $CH_3$ | $CH_3$ | $CH_3$ | |
| 3.018 | cyclopropyl | $CH_3$ | $C_2H_5$ | H | |
| 3.019 | cyclopropyl | $C_2H_5$ | $C_2H_5$ | H | |
| 3.020 | cyclopropyl | $nC_3H_7$ | $nC_3H_7$ | H | |

TABLE 3-continued

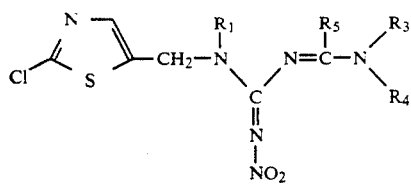

| Comp. No. | R₁ | R₄ | R₃ | R₅ | m.p. |
|---|---|---|---|---|---|
| 3.021 | cyclopropyl | $C_2H_5$ | $CH_3$ | $CH_3$ | |
| 3.022 | cyclopropyl | $C_2H_5$ | $C_2H_5$ | $CH_3$ | |
| 3.023 | $nC_3H_7$ | $CH_3$ | $CH_3$ | H | |
| 3.024 | $nC_3H_7$ | $C_2H_5$ | $C_2H_5$ | H | |
| 3.025 | $CH_3$ | —$CH_2CH_2CH_2CH_2$— | | H | |
| 3.026 | $CH_3$ | —$CH_2CH_2CH_2CH_2CH_2$— | | H | |
| 3.027 | H | $CH_3$ | $CH_3$ | $CH_3$ | |
| 3.028 | $CH_3$ | $CH_3$ | $CH_3$ | phenyl | |
| 3.029 | $CH_3$ | $CH_3$ | $CH_3$ | —$CH_2OCH_3$ | |
| 3.030 | $CH_3$ | $CH_3$ | $CH_3$ | —CN | |
| 3.031 | $CH_3$ | $CH_3$ | $CH_3$ | —$COOC_2H_5$ | |
| 3.032 | $CH_3$ | $CH_3$ | $CH_3$ | —$CON(CH_3)_2$ | |
| 3.033 | $CH_3$ | $CH_3$ | —$CH_2CH_2COOC_2H_5$ | H | |

TABLE 4

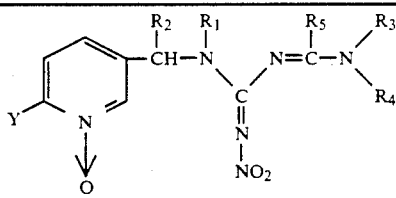

| Comp. No. | Y | R₁ | R₂ | R₃ | R₄ | R₅ | m.p. |
|---|---|---|---|---|---|---|---|
| 4.001 | Cl | $CH_3$ | H | $CH_3$ | $CH_3$ | H | |
| 4.002 | Cl | H | H | $CH_3$ | $CH_3$ | H | |
| 4.003 | Cl | $CH_3$ | H | $CH_3$ | $CH_3$ | $CH_3$ | |
| 4.004 | Cl | $CH_3$ | H | $C_2H_5$ | $C_2H_5$ | H | |
| 4.005 | Cl | H | H | $CH_3$ | $CH_3$ | $CH_3$ | |
| 4.006 | Cl | $CH_3$ | H | $C_2H_5$ | $C_2H_5$ | $CH_3$ | |
| 4.007 | Cl | $CH_3$ | $CH_3$ | $CH_3$ | $CH_3$ | H | |
| 4.008 | Cl | $C_2H_5$ | H | $CH_3$ | $CH_3$ | H | 52° C. |
| 4.009 | Cl | $C_2H_5$ | H | $CH_3$ | $CH_3$ | $CH_3$ | amorphous |
| 4.010 | Cl | $C_2H_5$ | H | $C_2H_5$ | $C_2H_5$ | H | |
| 4.011 | Cl | $C_2H_5$ | $CH_3$ | $CH_3$ | $CH_3$ | H | |
| 4.012 | Cl | cyclopropyl | H | $CH_3$ | $CH_3$ | H | 65° C. |
| 4.013 | Cl | cyclopropyl | H | $CH_3$ | $CH_3$ | $CH_3$ | |
| 4.014 | Cl | cyclopropyl | H | $C_2H_5$ | $C_2H_5$ | H | |
| 4.015 | Cl | cyclopropyl | $CH_3$ | $CH_3$ | $CH_3$ | H | |
| 4.016 | H | $CH_3$ | H | $CH_3$ | $CH_3$ | H | |

TABLE 4-continued

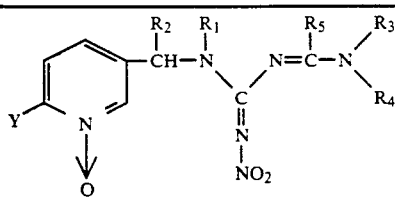

| Comp. No. | Y | $R_1$ | $R_2$ | $R_3$ | $R_4$ | $R_5$ | m.p. |
|---|---|---|---|---|---|---|---|
| 4.017 | H | $CH_3$ | H | $CH_3$ | $CH_3$ | $CH_3$ | |
| 4.018 | H | $CH_3$ | H | $C_2H_5$ | $C_2H_5$ | H | |
| 4.019 | H | H | H | $CH_3$ | $CH_3$ | H | |
| 4.020 | H | $C_2H_5$ | H | $CH_3$ | $CH_3$ | H | |
| 4.021 | H | ▷ | H | $CH_3$ | $CH_3$ | H | |
| 4.022 | Cl | $CH_3$ | H | $CH_3$ | $CH_3$ | ⌬ | |
| 4.023 | Cl | $CH_3$ | H | $CH_3$ | $CH_3$ | $-CH_2OCH_3$ | |
| 4.024 | Cl | $CH_3$ | H | $CH_3$ | $CH_3$ | $-CN$ | |
| 4.025 | Cl | $CH_3$ | H | $CH_3$ | $CH_3$ | $-COOC_2H_5$ | |
| 4.026 | Cl | $CH_3$ | H | $CH_3$ | $CH_3$ | $-CON(CH_3)_2$ | |
| 4.027 | Cl | $CH_3$ | H | $CH_3$ | $-CH_2CH_2COOC_2H_5$ | H | |

TABLE 5

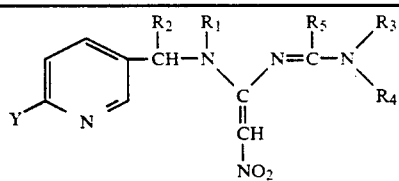

| Comp. No. | Y | $R_1$ | $R_2$ | $R_3$ | $R_4$ | $R_5$ | m.p. |
|---|---|---|---|---|---|---|---|
| 5.001 | Cl | $CH_3$ | H | $CH_3$ | $CH_3$ | H | 108–110° C. |
| 5.002 | Cl | H | H | $CH_3$ | $CH_3$ | H | |
| 5.003 | Cl | $CH_3$ | H | $CH_3$ | $CH_3$ | $CH_3$ | |
| 5.004 | Cl | $CH_3$ | H | $CH_3$ | $C_2H_5$ | H | |
| 5.005 | Cl | $CH_3$ | H | $C_2H_5$ | $C_2H_5$ | H | |
| 5.006 | Cl | $CH_3$ | H | $nC_3H_7$ | $nC_3H_7$ | H | |
| 5.007 | Cl | $CH_3$ | H | $C_2H_5$ | $CH_3$ | $CH_3$ | |
| 5.008 | Cl | H | H | $CH_3$ | $CH_3$ | $CH_3$ | |
| 5.009 | Cl | $CH_3$ | H | $C_2H_5$ | $C_2H_5$ | $CH_3$ | |
| 5.010 | Cl | $CH_3$ | $CH_3$ | $CH_3$ | $CH_3$ | H | |
| 5.011 | Cl | $CH_3$ | $CH_3$ | $C_2H_5$ | $C_2H_5$ | H | |
| 5.012 | Cl | $C_2H_5$ | H | $CH_3$ | $CH_3$ | H | 48–50° C. |
| 5.013 | Cl | $C_2H_5$ | H | $CH_3$ | $CH_3$ | $CH_3$ | |
| 5.014 | Cl | $C_2H_5$ | H | $CH_3$ | $C_2H_5$ | H | |
| 5.015 | Cl | $C_2H_5$ | H | $C_2H_5$ | $C_2H_5$ | H | |
| 5.016 | Cl | $C_2H_5$ | H | $nC_3H_7$ | $nC_3H_7$ | H | |
| 5.017 | Cl | $C_2H_5$ | H | $CH_3$ | $CH_3$ | $C_2H_5$ | |
| 5.018 | Cl | $C_2H_5$ | H | $CH_3$ | $CH_3$ | $CH_3$ | |
| 5.019 | Cl | $C_2H_5$ | H | $C_2H_5$ | $C_2H_5$ | $CH_3$ | |
| 5.020 | Cl | $C_2H_5$ | $CH_3$ | $CH_3$ | $CH_3$ | H | |
| 5.021 | Cl | $C_2H_5$ | $CH_3$ | $C_2H_5$ | $C_2H_5$ | H | |
| 5.022 | Cl | ▷ | H | $CH_3$ | $CH_3$ | H | amorphous |
| 5.023 | Cl | ▷ | H | $CH_3$ | $CH_3$ | $CH_3$ | |
| 5.024 | Cl | ▷ | H | $CH_3$ | $C_2H_5$ | H | |

TABLE 5-continued

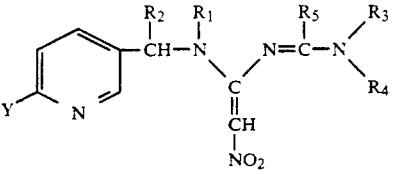

| Comp. No. | Y | R₁ | R₂ | R₃ | R₄ | R₅ | m.p. |
|---|---|---|---|---|---|---|---|
| 5.025 | Cl | ▷ | H | C₂H₅ | C₂H₅ | H | |
| 5.026 | Cl | ▷ | H | nC₃H₇ | nC₃H₇ | H | |
| 5.027 | Cl | ▷ | H | CH₃ | CH₃ | C₂H₅ | |
| 5.028 | Cl | ▷ | H | C₂H₅ | CH₃ | CH₃ | |
| 5.029 | Cl | ▷ | H | C₂H₅ | C₂H₅ | CH₃ | |
| 5.030 | Cl | ▷ | CH₃ | CH₃ | CH₃ | H | |
| 5.031 | Cl | ▷ | CH₃ | C₂H₅ | C₂H₅ | H | |
| 5.032 | Cl | nC₃H₇ | H | CH₃ | CH₃ | H | |
| 5.033 | Cl | nC₃H₇ | H | C₂H₅ | C₂H₅ | H | |
| 5.034 | Cl | CH₃ | H | —CH₂CH₂CH₂CH₂— | | H | |
| 5.035 | Cl | CH₃ | H | —CH₂CH₂CH₂CH₂CH₂— | | H | |
| 5.036 | Cl | H | CH₃ | CH₃ | CH₃ | H | |
| 5.037 | Cl | H | CH₃ | CH₃ | CH₃ | CH₃ | |
| 5.038 | H | CH₃ | H | CH₃ | CH₃ | H | |
| 5.039 | H | CH₃ | H | CH₃ | CH₃ | CH₃ | |
| 5.040 | H | CH₃ | H | C₂H₅ | C₂H₅ | H | |
| 5.041 | H | H | H | CH₃ | CH₃ | H | |
| 5.042 | H | C₂H₅ | H | CH₃ | CH₃ | H | |
| 5.043 | H | ▷ | H | CH₃ | CH₃ | H | |
| 5.044 | Cl | CH₃ | H | CH₃ | CH₃ | ⌬(phenyl) | |
| 5.045 | Cl | CH₃ | H | CH₃ | CH₃ | —CH₂OCH₃ | |
| 5.046 | Cl | CH₃ | H | CH₃ | CH₃ | —CN | |
| 5.047 | Cl | CH₃ | H | CH₃ | CH₃ | —COOC₂H₅ | |
| 5.048 | Cl | CH₃ | H | CH₃ | CH₃ | —CON(CH₃)₂ | |
| 5.049 | Cl | CH₃ | H | CH₃ | —CH₂CH₂COOC₂H₅ | H | |

TABLE 6

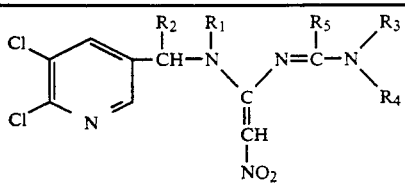

| Comp. No. | R1 | R2 | R3 | R4 | R5 | m.p. |
|---|---|---|---|---|---|---|
| 6.001 | $CH_3$ | H | $CH_3$ | $CH_3$ | H | |
| 6.002 | H | H | $CH_3$ | $CH_3$ | H | |
| 6.003 | $CH_3$ | H | $CH_3$ | $CH_3$ | $CH_3$ | |
| 6.004 | $CH_3$ | H | $CH_3$ | $C_2H_5$ | H | |
| 6.005 | $CH_3$ | H | $C_2H_5$ | $C_2H_5$ | H | |
| 6.006 | $CH_3$ | H | $nC_3H_7$ | $nC_3H_7$ | H | |
| 6.007 | $CH_3$ | H | $C_2H_5$ | $CH_3$ | $CH_3$ | |
| 6.008 | H | H | $CH_3$ | $CH_3$ | $CH_3$ | |
| 6.009 | $CH_3$ | H | $C_2H_5$ | $C_2H_5$ | $CH_3$ | |
| 6.010 | $CH_3$ | $CH_3$ | $CH_3$ | $CH_3$ | H | |
| 6.011 | $CH_3$ | $CH_3$ | $C_2H_5$ | $C_2H_5$ | H | |
| 6.012 | $C_2H_5$ | H | $CH_3$ | $CH_3$ | H | |
| 6.013 | $C_2H_5$ | H | $CH_3$ | $CH_3$ | $CH_3$ | |
| 6.014 | $C_2H_5$ | H | $CH_3$ | $C_2H_5$ | H | |
| 6.015 | $C_2H_5$ | H | $C_2H_5$ | $C_2H_5$ | H | |
| 6.016 | $C_2H_5$ | H | $nC_3H_7$ | $nC_3H_7$ | H | |
| 6.017 | $C_2H_5$ | H | $CH_3$ | $CH_3$ | $C_2H_5$ | |
| 6.018 | $C_2H_5$ | H | $C_2H_5$ | $CH_3$ | $CH_3$ | |
| 6.019 | $C_2H_5$ | H | $C_2H_5$ | $C_2H_5$ | $CH_3$ | |
| 6.020 | $C_2H_5$ | $CH_3$ | $CH_3$ | $CH_3$ | H | |
| 6.021 | $C_2H_5$ | $CH_3$ | $C_2H_5$ | $C_2H_5$ | H | |
| 6.022 | cyclopropyl | H | $CH_3$ | $CH_3$ | H | |
| 6.023 | cyclopropyl | H | $CH_3$ | $CH_3$ | $CH_3$ | |
| 6.024 | cyclopropyl | H | $CH_3$ | $C_2H_5$ | H | |
| 6.025 | cyclopropyl | H | $C_2H_5$ | $C_2H_5$ | H | |
| 6.026 | cyclopropyl | H | $nC_3H_7$ | $nC_3H_7$ | H | |
| 6.027 | cyclopropyl | H | $CH_3$ | $CH_3$ | $C_2H_5$ | |
| 6.028 | cyclopropyl | H | $C_2H_5$ | $CH_3$ | $CH_3$ | |
| 6.029 | cyclopropyl | H | $C_2H_5$ | $C_2H_5$ | $CH_3$ | |
| 6.030 | cyclopropyl | $CH_3$ | $CH_3$ | $CH_3$ | H | |
| 6.031 | cyclopropyl | $CH_3$ | $C_2H_5$ | $C_2H_5$ | H | |
| 6.032 | $nC_3H_7$ | H | $CH_3$ | $CH_3$ | H | |
| 6.033 | $nC_3H_7$ | H | $C_2H_5$ | $C_2H_5$ | H | |
| 6.034 | $CH_3$ | H | $-CH_2CH_2CH_2CH_2-$ | | H | |
| 6.035 | $CH_3$ | H | $-CH_2CH_2CH_2CH_2CH_2-$ | | H | |
| 6.036 | H | $CH_3$ | $CH_3$ | $CH_3$ | H | |

TABLE 6-continued

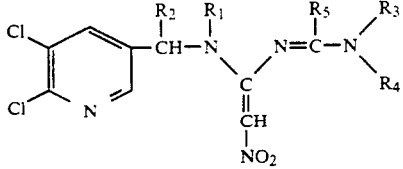

| Comp. No. | R₁ | R₂ | R₃ | R₄ | R₅ | m.p. |
|---|---|---|---|---|---|---|
| 6.037 | H | CH₃ | CH₃ | CH₃ | CH₃ | |
| 6.038 | CH₃ | H | CH₃ | CH₃ | 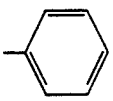 | |
| 6.039 | CH₃ | H | CH₃ | CH₃ | —CH₂OCH₃ | |
| 6.040 | CH₃ | H | CH₃ | CH₃ | —CN | |
| 6.041 | CH₃ | H | CH₃ | CH₃ | —COOC₂H₅ | |
| 6.042 | CH₃ | H | CH₃ | CH₃ | —CON(CH₃)₂ | |
| 6.043 | CH₃ | H | CH₃ | —CH₂CH₂COOC₂H₅ | H | |

TABLE 7

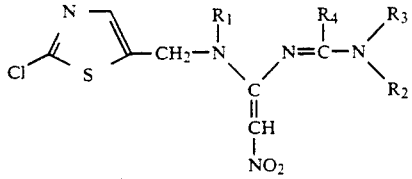

| Comp. No. | R₁ | R₂ | R₃ | R₄ | m.p. |
|---|---|---|---|---|---|
| 7.001 | CH₃ | CH₃ | CH₃ | H | amorphous |
| 7.002 | H | CH₃ | CH₃ | H | |
| 7.003 | CH₃ | CH₃ | CH₃ | CH₃ | |
| 7.004 | CH₃ | CH₃ | C₂H₅ | H | |
| 7.005 | CH₃ | C₂H₅ | C₂H₅ | H | |
| 7.006 | CH₃ | C₂H₅ | CH₃ | CH₃ | |
| 7.007 | CH₃ | C₂H₅ | C₂H₅ | CH₃ | |
| 7.008 | C₂H₅ | CH₃ | CH₃ | H | amorphous |
| 7.009 | C₂H₅ | CH₃ | CH₃ | CH₃ | |
| 7.010 | C₂H₅ | CH₃ | C₂H₅ | H | |
| 7.011 | C₂H₅ | C₂H₅ | C₂H₅ | H | |
| 7.012 | C₂H₅ | nC₃H₇ | nC₃H₇ | H | |
| 7.013 | C₂H₅ | CH₃ | CH₃ | C₂H₅ | |
| 7.014 | C₂H₅ | C₂H₅ | CH₃ | CH₃ | |
| 7.015 | C₂H₅ | C₂H₅ | C₂H₅ | CH₃ | |
| 7.016 |  | CH₃ | CH₃ | H | amorphous |
| 7.017 |  | CH₃ | CH₃ | CH₃ | |
| 7.018 |  | CH₃ | C₂H₅ | H | |
| 7.019 |  | C₂H₅ | C₂H₅ | H | |
| 7.020 |  | nC₃H₇ | nC₃H₇ | H | |
| 7.021 |  | C₂H₅ | CH₃ | CH₃ | |

TABLE 7-continued

| Comp. No. | R₁ | R₂ | R₃ | R₄ | m.p. |
|---|---|---|---|---|---|
| 7.022 | ▷ | C₂H₅ | C₂H₅ | CH₃ | |
| 7.023 | nC₃H₇ | CH₃ | CH₃ | H | |
| 7.024 | nC₃H₇ | C₂H₅ | C₂H₅ | H | |
| 7.025 | CH₃ | —CH₂CH₂CH₂CH₂— | | H | |
| 7.026 | CH₃ | —CH₂CH₂CH₂CH₂CH₂— | | H | |
| 7.027 | H | CH₃ | CH₃ | CH₃ | |
| 7.028 | CH₃ | CH₃ | CH₃ | phenyl | |
| 7.029 | CH₃ | CH₃ | CH₃ | —CH₂OCH₃ | |
| 7.030 | CH₃ | CH₃ | CH₃ | —CN | |
| 7.031 | CH₃ | CH₃ | CH₃ | —COOC₂H₅ | |
| 7.032 | CH₃ | CH₃ | CH₃ | —CON(CH₃)₂ | |
| 7.033 | CH₃ | CH₃ | —CH₂CH₂COOC₂H₅ | H | |

TABLE 8

| Comp. No. | Y | R₁ | R₂ | R₃ | R₄ | R₅ | m.p. |
|---|---|---|---|---|---|---|---|
| 8.001 | Cl | CH₃ | H | CH₃ | CH₃ | H | amorphous |
| 8.002 | Cl | H | H | CH₃ | CH₃ | H | |
| 8.003 | Cl | CH₃ | H | CH₃ | CH₃ | CH₃ | |
| 8.004 | Cl | CH₃ | H | C₂H₅ | C₂H₅ | H | |
| 8.005 | Cl | H | H | CH₃ | CH₃ | CH₃ | |
| 8.006 | Cl | CH₃ | H | C₂H₅ | C₂H₅ | CH₃ | |
| 8.007 | Cl | CH₃ | CH₃ | CH₃ | CH₃ | H | |
| 8.008 | Cl | C₂H₅ | H | CH₃ | CH₃ | H | amorphous |
| 8.009 | Cl | C₂H₅ | H | CH₃ | CH₃ | CH₃ | |
| 8.010 | Cl | C₂H₅ | H | C₂H₅ | C₂H₅ | H | |
| 8.011 | Cl | C₂H₅ | CH₃ | CH₃ | CH₃ | H | |
| 8.012 | Cl | ▷ | H | CH₃ | CH₃ | H | amorphous |
| 8.013 | Cl | ▷ | H | CH₃ | CH₃ | CH₃ | |
| 8.014 | Cl | ▷ | H | C₂H₅ | C₂H₅ | H | |
| 8.015 | Cl | ▷ | CH₃ | CH₃ | CH₃ | H | |
| 8.016 | H | CH₃ | H | CH₃ | CH₃ | H | |
| 8.017 | H | CH₃ | H | CH₃ | CH₃ | CH₃ | |
| 8.018 | H | CH₃ | H | C₂H₅ | C₂H₅ | H | |
| 8.019 | H | H | H | CH₃ | CH₃ | H | |
| 8.020 | H | C₂H₅ | H | CH₃ | CH₃ | H | |

TABLE 8-continued

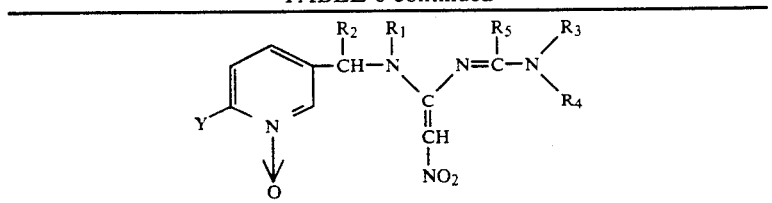

| Comp. No. | Y | $R_1$ | $R_2$ | $R_3$ | $R_4$ | $R_5$ | m.p. |
|---|---|---|---|---|---|---|---|
| 8.021 | H | ▷ | H | $CH_3$ | $CH_3$ | H | |
| 8.022 | Cl | $CH_3$ | H | $CH_3$ | $CH_3$ | ⌬ | |
| 8.023 | Cl | $CH_3$ | H | $CH_3$ | $CH_3$ | $-CH_2OCH_3$ | |
| 8.024 | Cl | $CH_3$ | H | $CH_3$ | $CH_3$ | $-CN$ | |
| 8.025 | Cl | $CH_3$ | H | $CH_3$ | $CH_3$ | $-COOC_2H_5$ | |
| 8.026 | Cl | $CH_3$ | H | $CH_3$ | $CH_3$ | $-CON(CH_3)_2$ | |
| 8.027 | Cl | $CH_3$ | H | $CH_3$ | $-CH_2CH_2COOC_2H_5$ | H | |

TABLE 9

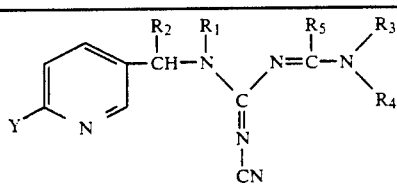

| Comp. No. | Y | $R_1$ | $R_2$ | $R_3$ | $R_4$ | $R_5$ | m.p. |
|---|---|---|---|---|---|---|---|
| 9.001 | Cl | $CH_3$ | H | $CH_3$ | $CH_3$ | H | 94-96° C. |
| 9.002 | Cl | H | H | $CH_3$ | $CH_3$ | H | |
| 9.003 | Cl | $CH_3$ | H | $CH_3$ | $CH_3$ | $CH_3$ | $n_D^{23} = 1.5559$ |
| 9.004 | Cl | $CH_3$ | H | $CH_3$ | $C_2H_5$ | H | |
| 9.005 | Cl | $CH_3$ | H | $C_2H_5$ | $C_2H_5$ | H | |
| 9.006 | Cl | $CH_3$ | H | $nC_3H_7$ | $nC_3H_7$ | H | |
| 9.007 | Cl | $CH_3$ | H | $C_2H_5$ | $CH_3$ | $CH_3$ | |
| 9.008 | Cl | H | H | $CH_3$ | $CH_3$ | $CH_3$ | |
| 9.009 | Cl | $CH_3$ | H | $C_2H_5$ | $C_2H_5$ | $CH_3$ | |
| 9.010 | Cl | $CH_3$ | $CH_3$ | $CH_3$ | $CH_3$ | H | |
| 9.011 | Cl | $CH_3$ | $CH_3$ | $C_2H_5$ | H | | |
| 9.012 | Cl | $C_2H_5$ | H | $CH_3$ | $CH_3$ | H | |
| 9.013 | Cl | $C_2H_5$ | H | $CH_3$ | $CH_3$ | $CH_3$ | |
| 0.014 | Cl | $C_2H_5$ | H | $CH_3$ | $C_2H_5$ | H | |
| 9.015 | Cl | $C_2H_5$ | H | $C_2H_5$ | $C_2H_5$ | H | |
| 9.016 | Cl | $C_2H_5$ | H | $nC_3H_7$ | $nC_3H_7$ | H | |
| 9.017 | Cl | $C_2H_5$ | H | $CH_3$ | $CH_3$ | $C_2H_5$ | |
| 9.018 | Cl | $C_2H_5$ | H | $C_2H_5$ | $CH_3$ | $CH_3$ | |
| 9.019 | Cl | $C_2H_5$ | H | $C_2H_5$ | $C_2H_5$ | $CH_3$ | |
| 9.020 | Cl | $C_2H_5$ | $CH_3$ | $CH_3$ | $CH_3$ | H | |
| 9.021 | Cl | $C_2H_5$ | $CH_3$ | $C_2H_5$ | $C_2H_5$ | H | |
| 9.022 | Cl | ▷ | H | $CH_3$ | $CH_3$ | H | |
| 9.023 | Cl | ▷ | H | $CH_3$ | $CH_3$ | $CH_3$ | |
| 9.024 | Cl | ▷ | H | $CH_3$ | $C_2H_5$ | H | |
| 9.025 | Cl | ▷ | H | $C_2H_5$ | $C_2H_5$ | H | |

TABLE 9-continued

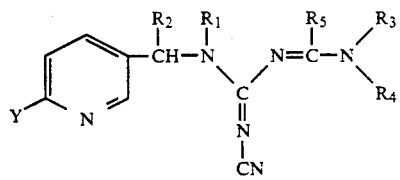

| Comp. No. | Y | R₁ | R₂ | R₃ | R₄ | R₅ | m.p. |
|---|---|---|---|---|---|---|---|
| 9.026 | Cl | cyclopropyl | H | $nC_3H_7$ | $nC_3H_7$ | H | |
| 9.027 | Cl | cyclopropyl | H | $CH_3$ | $CH_3$ | $C_2H_5$ | |
| 9.028 | Cl | cyclopropyl | H | $C_2H_5$ | $CH_3$ | $CH_3$ | |
| 9.029 | Cl | cyclopropyl | H | $C_2H_5$ | $C_2H_5$ | $CH_3$ | |
| 9.030 | Cl | cyclopropyl | $CH_3$ | $CH_3$ | $CH_3$ | H | |
| 9.031 | Cl | cyclopropyl | $CH_3$ | $C_2H_5$ | $C_2H_5$ | H | |
| 9.032 | Cl | $nC_3H_7$ | H | $CH_3$ | $CH_3$ | H | |
| 9.033 | Cl | $nC_3H_7$ | H | $C_2H_5$ | $C_2H_5$ | H | |
| 9.034 | Cl | $CH_3$ | H | $-CH_2CH_2CH_2CH_2-$ | | H | |
| 9.035 | Cl | $CH_3$ | H | $-CH_2CH_2CH_2CH_2CH_2-$ | | H | |
| 9.036 | Cl | H | $CH_3$ | $CH_3$ | $CH_3$ | H | |
| 9.037 | Cl | H | $CH_3$ | $CH_3$ | $CH_3$ | $CH_3$ | |
| 9.038 | H | $CH_3$ | H | $CH_3$ | $CH_3$ | H | $n_D^{23} = 1.5859$ |
| 9.039 | H | $CH_3$ | H | $CH_3$ | $CH_3$ | $CH_3$ | |
| 9.040 | H | $CH_3$ | H | $C_2H_5$ | $C_2H_5$ | H | |
| 9.041 | H | H | H | $CH_3$ | $CH_3$ | H | |
| 9.042 | H | $C_2H_5$ | H | $CH_3$ | $CH_3$ | H | |
| 9.043 | H | cyclopropyl-H | | $CH_3$ | $CH_3$ | H | |
| 9.044 | Cl | $CH_3$ | H | $CH_3$ | $CH_3$ | phenyl | |
| 9.045 | Cl | $CH_3$ | H | $CH_3$ | $CH_3$ | $-CH_2OCH_3$ | |
| 9.046 | Cl | $CH_3$ | H | $CH_3$ | $CH_3$ | $-CN$ | |
| 9.047 | Cl | $CH_3$ | H | $CH_3$ | $CH_3$ | $-COOC_2H_5$ | |
| 9.048 | Cl | $CH_3$ | H | $CH_3$ | $CH_3$ | $-CON(CH_3)_2$ | |
| 9.049 | Cl | $CH_3$ | H | $CH_3$ | $-CH_2CH_2COOC_2H_5$ | H | |

TABLE 10

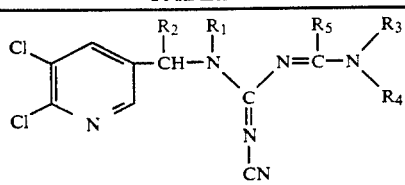

| Comp. No. | R₁ | R₂ | R₃ | R₄ | R₅ | m.p. |
|---|---|---|---|---|---|---|
| 10.001 | CH₃ | H | CH₃ | CH₃ | H | 117–120° C. |
| 10.002 | H | H | CH₃ | CH₃ | H | |
| 10.003 | CH₃ | H | CH₃ | CH₃ | CH₃ | $n_D^{23} = 1.5802$ |
| 10.004 | CH₃ | H | CH₃ | C₂H₅ | H | |
| 10.005 | CH₃ | H | C₂H₅ | C₂H₅ | H | |
| 10.006 | CH₂ | H | nC₃H₇ | H | | |
| 10.007 | CH₃ | H | C₂H₅ | CH₃ | CH₃ | |
| 10.008 | H | H | CH₃ | CH₃ | CH₃ | |
| 10.009 | CH₃ | H | C₂H₅ | C₂H₅ | CH₃ | |
| 10.010 | CH₃ | CH₃ | CH₃ | CH₃ | H | |
| 10.011 | CH₃ | CH₃ | C₂H₅ | C₂H₅ | H | |
| 10.012 | C₂H₅ | H | CH₃ | CH₃ | H | 102–103° C. |
| 10.013 | C₂H₅ | H | CH₃ | CH₃ | CH₃ | |
| 10.014 | C₂H₅ | H | CH₃ | C₂H₅ | H | |
| 10.015 | C₂H₅ | H | C₂H₅ | C₂H₅ | H | |
| 10.016 | C₂H₅ | H | nC₃H₇ | nC₃H₇ | H | |
| 10.017 | C₂H₅ | H | CH₃ | CH₃ | C₂H₅ | |
| 10.018 | C₂H₅ | H | C₂H₅ | CH₃ | CH₃ | |
| 10.019 | C₂H₅ | H | C₂H₅ | C₂H₅ | CH₃ | |
| 10.020 | C₂H₅ | CH₃ | CH₃ | CH₃ | H | |
| 10.021 | C₂H₅ | CH₃ | C₂H₅ | C₂H₅ | H | |
| 10.022 | cyclopropyl | H | CH₃ | CH₃ | H | |
| 10.023 | cyclopropyl | H | CH₃ | CH₃ | CH₃ | |
| 10.024 | cyclopropyl | H | CH₃ | C₂H₅ | H | |
| 10.025 | cyclopropyl | H | C₂H₅ | C₂H₅ | H | |
| 10.026 | cyclopropyl | H | nC₃H₇ | nC₃H₇ | H | |
| 10.027 | cyclopropyl | H | CH₃ | CH₃ | C₂H₅ | |
| 10.028 | cyclopropyl | H | C₂H₅ | CH₃ | CH₃ | |
| 10.029 | cyclopropyl | H | C₂H₅ | C₂H₅ | CH₃ | |
| 10.030 | cyclopropyl | CH₃ | CH₃ | CH₃ | H | |
| 10.031 | cyclopropyl | CH₃ | C₂H₅ | C₂H₅ | H | |
| 10.032 | nC₃H₇ | H | CH₃ | CH₃ | H | |
| 10.033 | nC₃H₇ | H | C₂H₅ | C₂H₅ | H | |
| 10.034 | CH₃ | H | —CH₂CH₂CH₂CH₂— | | H | |
| 10.035 | CH₃ | H | —CH₂CH₂CH₂CH₂CH₂— | | H | |

TABLE 10-continued

| Comp. No. | R₁ | R₂ | R₃ | R₄ | R₅ | m.p. |
|---|---|---|---|---|---|---|
| 10.036 | H | CH₃ | CH₃ | CH₃ | H | |
| 10.037 | H | CH₃ | CH₃ | CH₃ | CH₃ | |
| 10.038 | CH₃ | H | CH₃ | CH₃ | 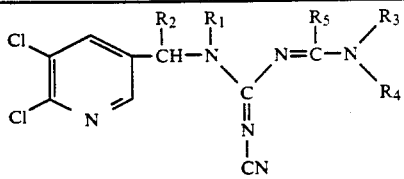 | |
| 10.039 | CH₃ | H | CH₃ | CH₃ | —CH₂OCH₃ | |
| 10.040 | CH₃ | H | CH₃ | CH₃ | —CN | |
| 10.041 | CH₃ | H | CH₃ | CH₃ | —COOC₂H₅ | |
| 10.042 | CH₃ | H | CH₃ | CH₃ | —CON(CH₃)₂ | |
| 10.043 | CH₃ | H | CH₃ | —CH₂CH₂COOC₂H₅ | H | |

TABLE 11

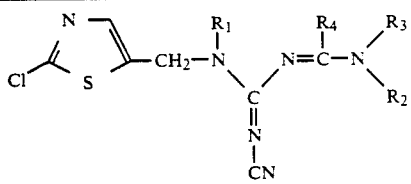

| Comp. No. | R₁ | R₂ | R₃ | R₄ | m.p. |
|---|---|---|---|---|---|
| 11.001 | CH₃ | CH₃ | CH₃ | H | |
| 11.002 | H | CH₃ | CH₃ | H | |
| 11.003 | CH₃ | CH₃ | CH₃ | CH₃ | |
| 11.004 | CH₃ | CH₃ | C₂H₅ | H | |
| 11.005 | CH₃ | C₂H₅ | C₂H₅ | H | |
| 11.006 | CH₃ | C₂H₅ | CH₃ | CH₃ | |
| 11.007 | CH₃ | C₂H₅ | C₂H₅ | CH₃ | |
| 11.008 | C₂H₅ | CH₃ | CH₃ | H | |
| 11.009 | C₂H₅ | CH₃ | CH₃ | CH₃ | |
| 11.010 | C₂H₅ | CH₃ | C₂H₅ | H | |
| 11.011 | C₂H₅ | C₂H₅ | C₂H₅ | H | |
| 11.012 | C₂H₅ | nC₃H₇ | nC₃H₇ | H | |
| 11.013 | C₂H₅ | CH₃ | CH₃ | C₂H₅ | |
| 11.014 | C₂H₅ | C₂H₅ | CH₃ | CH₃ | |
| 11.015 | C₂H₅ | C₂H₅ | C₂H₅ | CH₃ | |
| 11.016 | ▷ | CH₃ | CH₃ | H | |
| 11.017 | ▷ | CH₃ | CH₃ | CH₃ | |
| 11.018 | ▷ | CH₃ | C₂H₅ | H | |
| 11.019 | ▷ | C₂H₅ | C₂H₅ | H | |
| 11.020 | ▷ | nC₃H₇ | nC₃H₇ | H | |
| 11.021 | ▷ | C₂H₅ | CH₃ | CH₃ | |

TABLE 11-continued

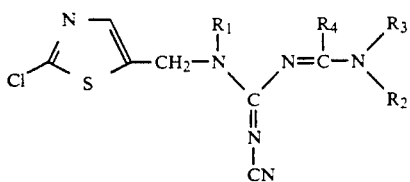

| Comp. No. | R₁ | R₂ | R₃ | R₄ | m.p. |
|---|---|---|---|---|---|
| 11.022 | △ | C₂H₅ | C₂H₅ | CH₃ | |
| 11.023 | nC₃H₇ | CH₃ | CH₃ | H | |
| 11.024 | nC₃H₇ | C₂H₅ | C₂H₅ | H | |
| 11.025 | CH₃ | —CH₂CH₂CH₂CH₂— | | H | |
| 11.026 | CH₃ | —CH₂CH₂CH₂CH₂CH₂— | | H | |
| 11.027 | H | CH₃ | CH₃ | CH₃ | |
| 11.028 | CH₃ | CH₃ | CH₃ | —C₆H₅ | |
| 11.029 | CH₃ | CH₃ | CH₃ | —CH₂OCH₃ | |
| 11.030 | CH₃ | CH₃ | CH₃ | —CN | |
| 11.031 | CH₃ | CH₃ | CH₃ | —COOC₂H₅ | |
| 11.032 | CH₃ | CH₃ | CH₃ | —CON(CH₃)₂ | |
| 11.033 | CH₃ | CH₃ | —CH₂CH₂COOC₂H₅ | H | |

TABLE 12

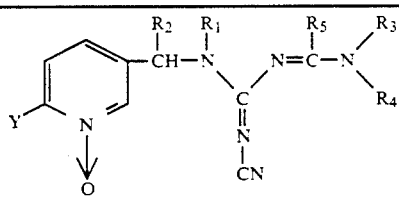

| Comp. No. | Y | R₁ | R₂ | R₃ | R₄ | R₅ | m.p. |
|---|---|---|---|---|---|---|---|
| 12.001 | Cl | CH₃ | H | CH₃ | CH₃ | H | |
| 12.002 | Cl | H | H | CH₃ | CH₃ | H | |
| 12.003 | Cl | CH₃ | H | CH₃ | CH₃ | CH₃ | |
| 12.004 | Cl | CH₃ | H | C₂H₅ | C₂H₅ | H | |
| 12.005 | Cl | H | H | CH₃ | CH₃ | CH₃ | |
| 12.006 | Cl | CH₃ | H | C₂H₅ | C₂H₅ | CH₃ | |
| 12.007 | Cl | CH₃ | CH₃ | CH₃ | CH₃ | H | |
| 12.008 | Cl | C₂H₅ | H | CH₃ | CH₃ | H | |
| 12.009 | Cl | C₂H₅ | H | CH₃ | CH₃ | CH₃ | |
| 12.010 | Cl | C₂H₅ | H | C₂H₅ | C₂H₅ | H | |
| 12.011 | Cl | C₂H₅ | CH₃ | CH₃ | CH₃ | H | |
| 12.012 | Cl | △ | H | CH₃ | CH₃ | H | |
| 12.013 | Cl | △ | H | CH₃ | CH₃ | CH₃ | |
| 12.014 | Cl | △ | H | C₂H₅ | C₂H₅ | H | |
| 12.015 | Cl | △ | CH₃ | CH₃ | CH₃ | H | |
| 12.016 | H | CH₃ | H | CH₃ | CH₃ | H | |
| 12.017 | H | CH₃ | H | CH₃ | CH₃ | CH₃ | |
| 12.018 | H | CH₃ | H | C₂H₅ | C₂H₅ | H | |
| 12.019 | H | H | H | CH₃ | CH₃ | H | |
| 12.020 | H | C₂H₅ | H | CH₃ | CH₃ | H | |

TABLE 12-continued

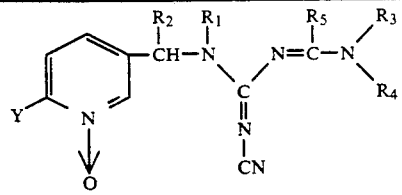

| Comp. No. | Y | R₁ | R₂ | R₃ | R₄ | R₅ | m.p. |
|---|---|---|---|---|---|---|---|
| 12.021 | H | cyclopropyl | H | CH₃ | CH₃ | H | |
| 12.022 | Cl | CH₃ | H | CH₃ | CH₃ | phenyl | |
| 12.023 | Cl | CH₃ | H | CH₃ | CH₃ | —CH₂OCH₃ | |
| 12.024 | Cl | CH₃ | H | CH₃ | CH₃ | —CN | |
| 12.025 | Cl | CH₃ | H | CH₃ | CH₃ | —COOC₂H₅ | |
| 12.026 | Cl | CH₃ | H | CH₃ | CH₃ | —CON(CH₃)₂ | |
| 12.027 | Cl | CH₃ | H | CH₃ | —CH₂CH₂COOC₂H₅ | H | |

TABLE 13

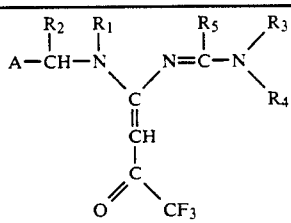

| Comp. No. | A | R₁ | R₂ | R₃ | R₄ | R₅ | m.p. |
|---|---|---|---|---|---|---|---|
| 13.001 | 2-Cl-pyridin-5-yl | CH₃ | H | CH₃ | CH₃ | H | |
| 13.002 | 2,3-diCl-pyridin-5-yl | CH₃ | H | CH₃ | CH₃ | H | |
| 13.003 | 2-Cl-pyridin-5-yl N-oxide | CH₃ | H | CH₃ | CH₃ | H | |
| 13.04 | 2-Cl-4-methylthiazol-5-yl | CH₃ | H | CH₃ | CH₃ | H | |

FORMULATION EXAMPLES (THROUGHOUT, PERCENTAGES ARE BY WEIGHT)

| Example F1: Emulsifiable concentrates | a) | b) | c) |
|---|---|---|---|
| compound no. 1.003 | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| Example F2: Solutions | a) | b) | c) | d) |
|---|---|---|---|---|
| compound no. 9.038 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160-190° C.) | — | — | 94% | — |

These solutions are suitable for application in the form of micro-drops.

| Example F3: Granules | a) | b) | c) | d) |
|---|---|---|---|---|
| compound no. 9.003 | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in methylene chloride, the solution is sprayed onto the carrier, and the solvent is subsequently evaporated off in vacuo.

| Example F4: Dusts | a) | b) |
|---|---|---|
| compound no. 9.003 | 2% | 5% |
| highly dispersed silicic acid | 1% | 5% |
| talcum | 97% | — |

| Example F4: Dusts | a) | b) |
|---|---|---|
| kaolin | — | 90% |

Ready-for-use dusts are obtained by intimately mixing the carriers with the active ingredient.

| Example F5: Wettable powders | a) | b) | c) |
|---|---|---|---|
| compound no. 1.001, 1.002, 1.003, 1.038 or 9.001 | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7-8 mol of ethylene oxide) | — | 2% | — |
| highly dispersed silicic acid | 5% | 10% | 10% |
| kaolin | 62% | 27% | — |

The active ingredient or active ingredient combination is mixed with the adjuvants and the mixture is thoroughly ground in a suitable mill, affording wettable powders which can be diluted with water to give suspensions of the desired concentration.

| Example F6: Emulsifiable concentrate | |
|---|---|
| compound no. 1.001, 1.002, 1.003, 1.038 or 9.001 | 10% |
| octylphenol polyethylene glycol ether (4-5 mol of ethylene oxide) | 3% |
| calcium dodecylbenzenesulfonate | 3% |
| castor oil polyglycol ether (36 mol of ethylene oxide) | 4% |
| cyclohexanone | 30% |
| xylene mixture | 50% |

Emulsions of any required concentration can be obtained from this concentrate by dilution with water.

| Example F7: Dusts | a) | b) |
|---|---|---|
| compound no. 1.001, 1.002, 1.003, 1.038 or 9.001 | 5% | 8% |
| talcum | 95% | — |
| kaolin | — | 92% |

Ready-for-use dusts are obtained by mixing the active ingredient with the carrier and grinding the mixture in a suitable mill.

| Example F8: Extruder granules | |
|---|---|
| compound no. 1.001, 1.002, 1.003, 1.038 or 9.001 | 10% |
| sodium lignosulfonate | 2% |
| carboxymethylcellulose | 1% |
| kaolin | 87% |

The active ingredient or the active ingredient combination is mixed and ground with the adjuvants and the mixture is moistened with water. The mixture is extruded, granulated and then dried in a stream of air.

| Example F9: Coated granules | |
|---|---|
| compound no. 1.001, 1.002, 1.003, 1.038 or 9.001 | 3% |
| polyethylene glycol (mol. wt. 200) | 3% |
| kaolin | 94% |

The finely ground active ingredient or the active ingredient combination is uniformly applied, in a mixer, to the kaolin moistened with polyethylene glycol. Non-dusty coated granules are obtained in this manner.

| Example F10: Suspension concentrate | |
|---|---|
| compound no. 1.001, 1.002, 1.003, 1.038 or 9.001 | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| silicone oil in the form of a 75% aqueous emulsion | 1% |
| water | 32% |

The finely ground active ingredient or the active ingredient combination is intimately mixed with the adjuvants, giving a suspension concentrate from which suspensions of any desired concentration can be obtained by dilution with water.

BIOLOGICAL EXAMPLES

Example B1

Action against Nilaparvata lugens

Rice plants are treated with an aqueous emulsion spray mixture comprising 400 ppm of the test compound. After the spray coating has dried, the rice plants are populated with cicada larvae in the 2nd and 3rd stages. Evaluation is made 21 days later. The percentage reduction in the population (% activity) is determined by comparing the number of surviving cicadas on the treated plants with that on untreated plants.

Compounds of Tables 1 to 13 exhibit good activity against Nilaparvata lugens in this test. In particular, compounds 1.001, 1.022, 1.038, 5.001 and 9.001 are more than 80% effective.

Example B2

Action against Nephotettix cincticeps

Rice plants are treated with an aqueous emulsion spray mixture comprising 400 ppm of the test compound. After the spray coating has dried, the rice plants are populated with cicada larvae in the 2nd and 3rd stages. Evaluation is made 21 days later. The percentage reduction in the population (% activity) is determined by comparing the number of surviving cicadas on the treated plants with that on untreated plants.

Compounds of Tables 1 to 13 exhibit good activity against Nephotettix cincticeps in this test. In particular, compounds 1.001, 1.022 and 5.001 are more than 80% effective.

Example B3

Action against Bemisia tabaci

Dwarf bean plants are placed in gauze cages and populated with adults of Bemisia tabaci (whitefly). When oviposition has taken place, all the adults are removed and 10 days later the plants and the nymphs located thereon are treated with an aqueous emulsion spray mixture of the test compounds (concentration 400 ppm). Evaluation is made 14 days after application of the test compound by determining the % hatching rate in comparison with untreated controls.

In this test, compounds of Tables 1 to 13 exhibit good activity against Bemisia tabaci. In particular, compounds 1.001 and 5.001 are more than 80% effective.

Example B4

Action against Aphis craccivora

Pea seedlings are infested with Aphis craccivora and then sprayed with a spray mixture comprising 400 ppm of the test compound, and incubated at 20° C. Evaluation is made 3 and 6 days later. The percentage reduction in the population (% activity) is determined by comparing the number of dead aphids on the treated plants with that on untreated plants. Compounds of Tables 1 to 13 exhibit good activity against Aphis craccivora in this test. In particular, compounds 1.001, 1.003, 1.012, 1.022, 1.038, 5.001 and 9.001 are more than 80% effective.

Example B5

Action against Myzus persicae

Pea seedlings are infested with Myzus persicae and then sprayed with a spray mixture comprising 400 ppm of the test compound, and incubated at 20° C. Evaluation is made 3 and 6 days later. The percentage reduction in the population (% activity) is determined by comparing the number of dead aphids on the treated plants with that on untreated plants. Compounds of Tables 1 to 13 exhibit good activity against Myzus persicae in this test. In particular, compounds 1.001 and 1.022 are more than 80% effective.

Example B6

Systemic action against Myzus persicae

Pea seedlings are infested with Myzus persicae and then placed with their roots in a spray mixture comprising 400 ppm of the test compound, and incubated at 20° C. Evaluation is made 3 and 6 days later. The percentage reduction in the population (% activity) is determined by comparing the number of dead aphids on the treated plants with that on untreated plants.

Compounds of Tables 1 to 13 exhibit good activity against Myzus persicae in this test. In particular, compounds 1.001, 1.003, 1.012, 1.022, 1.038 and 5.001 are more than 80% effective.

Example B7

Systemic action against Nilaparvata lugens

Pots containing rice plants are placed in an aqueous emulsion solution comprising 400 ppm of the test compound. The rice plants are then populated with larvae in the 2nd and 3rd stages. Evaluation is made 6 days later. The percentage reduction in the population (% activity) is determined by comparing the number of cicadas on the treated plants with that on untreated plants.

Compounds of Tables 1 to 13 exhibit good activity against Nilaparvata lugens in this test. In particular, compounds 1.001, 1.012, 1.022, 1.038, 3.001, 5.001 and 9.001 are more than 80% effective.

Example B8

Systemic action against Nephotettix cincticeps

Pots containing rice plants are placed in an aqueous emulsion solution comprising 400 ppm of the test compound. The rice plants are then populated with larvae in the 2nd and 3rd stages. Evaluation is made 6 days later. The percentage reduction in the population (% activity) is determined by comparing the number of cicadas on the treated plants with that on untreated plants.

Compounds of Tables 1 to 13 exhibit good activity against Nephotettix cincticeps in this test. In particular, compounds 1.001, 1.012, 1.022, 3.001, 5.001 and 9.001 are more than 80% effective.

Example B9

Feeding action against Ctenocephalides felis (systemic) 20 adult fleas of the species Ctenocephalides felis are placed in a flat round cage which is closed at both ends with gauze. A container that is closed at the bottom by a parafilm membrane is then placed on the cage. The container contains blood which comprises 50 ppm of the test compound and is kept at a constant temperature of 37° C. The fleas ingest the blood through the membrane. Evaluation is made 24 and 48 hours after the start. The percentage reduction in the population (% activity) is determined by comparing the number of dead fleas having treated blood with that having untreated blood. 24 hours after treatment the blood is replaced with fresh, likewise treated blood.

Compounds of Tables 1 to 13 exhibit good activity against Ctenocephalides felis in this test. In particular, compounds 1.001 and 5.001 are more than 80% effective.

What is claimed is:

1. A compound of the formula

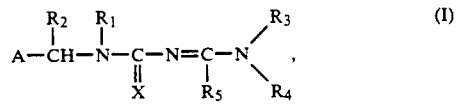

wherein
$R_1$ is hydrogen, $C_1$-$C_4$alkyl or $C_3$-$C_6$cycloalkyl,
$R_2$ is hydrogen or $C_1$-$C_4$alkyl,
$R_3$ is hydrogen, $C_1$-$C_4$alkyl or $C_3$-$C_6$cycloalkyl and
$R_4$ is $C_1$-$C_4$alkyl, $C_3$-$C_6$cycloalkyl or —CH$_2$CH$_2$COOR$_7$, or
$R_3$ and $R_4$ together are —(CH$_2$)$_4$— or —(CH$_2$)$_5$—,
$R_5$ is hydrogen, $C_1$-$C_4$alkyl,

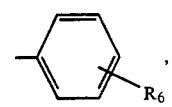

—CH$_2$OCH$_3$, —CN, —COOR$_7$ or

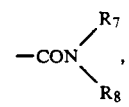

$R_6$ is hydrogen, chlorine, methyl or nitro,
$R_7$ and $R_8$ are each methyl or ethyl,
A is an unsubstituted or mono- to tetra-substituted pyridyl radical, one or two substituents being selected from the group consisting of $C_1$-$C_3$haloalkyl, cyclopropyl, halocyclopropyl, $C_2$-$C_3$alkenyl, $C_2$-$C_3$alkynyl, $C_2$-$C_3$haloalkenyl, $C_2$-$C_3$haloalkynyl, $C_1$-$C_3$haloalkoxy, $C_1$-$C_3$alkylthio, $C_1$-$C_3$haloalkylthio, allyloxy, propargyloxy, allylthio, propargylthio, haloallyloxy, haloallylthio, cyano and nitro, and/or from one to four substituents being selected from the group consisting of $C_1$-C-

$_3$alkyl, C$_1$-C$_3$alkoxy and halogen, and =X is =N—NO$_2$, in free form or in the form of an acid addition salt.

2. A compound according to claim 1 of formula I in free form.

3. A compound according to claim 2 of formula I, wherein the radical A is pyrid-3-yl, 2-halopyrid-5-yl or 2,3-dihalopyrid-5-yl.

4. A compound according to claim 3 of formula I, wherein R$_1$ is hydrogen, C$_1$-C$_3$alkyl or cyclopropyl, R$_2$ is hydrogen or methyl, R$_3$ is C$_1$-C$_3$alkyl and R$_4$ is C$_1$-C$_3$alkyl or ethoxycarbonylethyl, or R$_3$ and R$_4$ together are —(CH$_2$)$_4$— or —(CH$_2$)$_5$—, and R$_5$ is hydrogen, methyl, ethyl, phenyl, —CH$_2$OCH$_3$, —CN, —COOC$_2$H$_5$ or

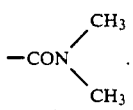

5. A compound according to claim 4 of formula I, wherein R$_1$ is methyl, ethyl or cyclopropyl, R$_2$ is hydrogen, R$_3$ is methyl, R$_4$ is methyl and R$_5$ is hydrogen or methyl.

6. A compound according to claim 5 of formula I, wherein the radical A is 2-chloropyrid-5-yl.

7. A compound according to claim 1 being N-(2-Chloropyrid-5-ylmethyl)-N-methyl-N'-(N,N-dimethylaminomethylene)-N''-nitroguanidine, in free form or in the form of an acid addition salt.

8. A compound according to claim 1 being selected from the group consisting of the compounds N-(2-chloropyrid-5-ylmethyl)N-methyl-N'-[1-(N,N-dimethylamino)ethylidene]-N''-nitroguanidine,
N-pyrid-3-ylmethyl-N-methyl-N'-(N,N-dimethylaminomethylene)-N''-nitroguanidine and
N-(2-chloropyrid-5-ylmethyl)N-ethyl-N'-(N,N-dimethylaminomethylene)-N''-nitroguanidine, in each case in free form or in the form of an acid addition salt.

9. A pesticidal composition, which comprises, as active ingredient, at least one compound according to claim 1 of formula I, in free form or in the form of an agrochemically acceptable acid addition salt, in an insecticidally or arachnidicidally effective amount, and at least one adjuvant.

10. A composition according to claim 9 for controlling insects or arachnids, which comprises, as carrier material, seeds of useful crops.

11. A method of controlling pests selected from insects and arachnids, which comprises applying, as active ingredient, to said pests or their locus at least one compound according to claim 1 of formula I, in free form or in the form of an agrochemically acceptable acid addition salt, in an insecticidally or arachnidicidally effective amount.

12. A method of protecting seeds from pests selected from insects and arachnids, which comprises treating the seeds or a furrow in which they are planted with an insecticidally or arachnidicidally effective amount of a compound according to claim 1 of formula I, in free form or in the form of an agrochemically acceptable acid addition salt.

13. A compound according to claim 1 being N-(2-Chloropyrid-5-ylmethyl)-N-cyclopropyl-N'-(N,N-dimethylaminomethylene)-N''-nitroguanidine, in free form or in the form of an acid addition salt.

* * * * *